(12) United States Patent
De Los Santos et al.

(10) Patent No.: US 11,912,751 B2
(45) Date of Patent: Feb. 27, 2024

(54) BI-FUNCTIONAL FUSION PROTEINS COMPRISED OF TGF-B AND IMMUNE CHECKPOINT DOMAINS

(71) Applicant: Samuel Dequina Bernal, Woodland Hills, CA (US)

(72) Inventors: Marvin Ilacas De Los Santos, Makati (PH); Samuel Dequina Bernal, Woodland Hills, CA (US)

(73) Assignee: Globetek Science Foundation, Makati (PH)

(*) Notice: Subject to any disclaimer, the term of this patent is extended or adjusted under 35 U.S.C. 154(b) by 43 days.

(21) Appl. No.: 17/248,288

(22) Filed: Jan. 19, 2021

(65) Prior Publication Data
US 2021/0238245 A1  Aug. 5, 2021

Related U.S. Application Data

(60) Provisional application No. 62/968,664, filed on Jan. 31, 2020.

(51) Int. Cl.
C07K 14/495 (2006.01)
A61K 38/00 (2006.01)

(52) U.S. Cl.
CPC ............ *C07K 14/495* (2013.01); *A61K 38/00* (2013.01); *C07K 2319/30* (2013.01)

(58) Field of Classification Search
None
See application file for complete search history.

(56) References Cited

U.S. PATENT DOCUMENTS

2013/0039911 A1* 2/2013 Bedi .................... A61K 31/704
530/391.1

* cited by examiner

Primary Examiner — Elizabeth C. Kemmerer

(57) ABSTRACT

This invention discloses a bifunctional TGF-B/immune checkpoint fusion gene and protein with anti-inflammatory activity that represents a new class of therapy for Immune disorders, immune dysregulation, and autoimmune diseases. The bifunctional TGF-B/immune checkpoint fusion gene and protein include: (i) a TGF-B domain consists of TGF-B1 (ii) an immune checkpoint consisting of PD-L1, (iii) a flexible peptide linker that links two TGF-B domains resulting in a dimeric TGF-B construct wherein the dimeric form of the TGF-B ligand is important for its binding and functional activity, and (iv) a rigid peptide linker, wherein the dimeric TGF-B ligand is linked to the immune checkpoint ligand.

A unique feature of this invention is the engineering of a dimeric TGF-B1 domain in the TGF-B1/PD-L1 fusion protein which was experimentally shown to be important in its binding to its TFGBR1 receptor and its functional activity. The functional domains of the fusion prot

Fig. 1A

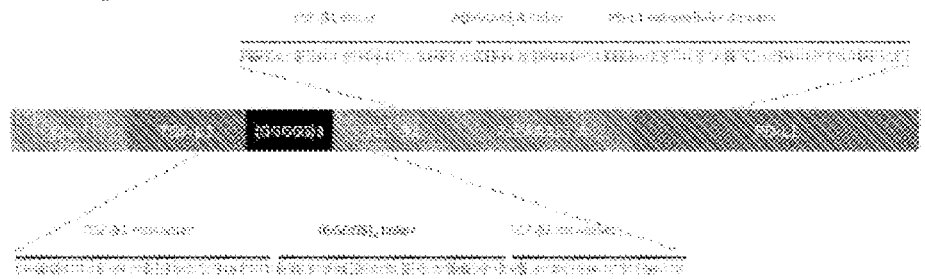

Fig. 1B

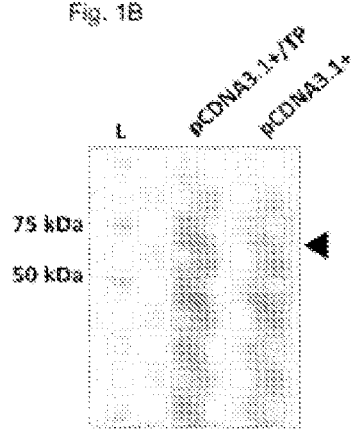

Fig. 1C

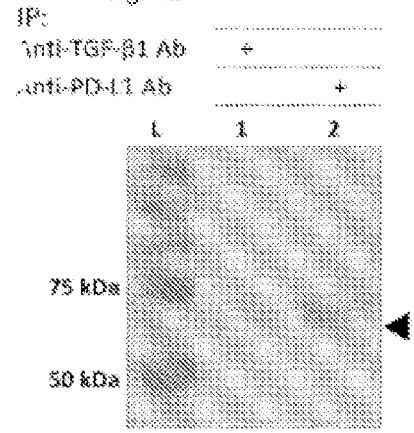

Fig. 1D

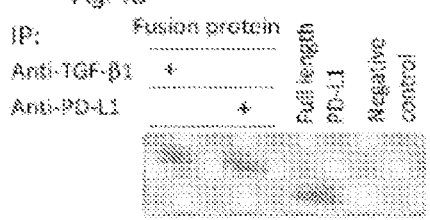

Fig. 1E

Figure 1. Development of a novel TGF-B1/PD-L1 fusion protein. A) Schematic representation of fusion gene construct. B) SDS-PAGE profile of HEK 293 cells transfected with the fusion gene. C) Immunoprecipitation (IP) of fusion protein. D) Molecular weight comparison between the fusion protein and mammalian-derived full-length PD-L1 protein. E) Schematic representation of the TGF-B1/PD-L1 fusion protein (SEQ ID NO: 13).

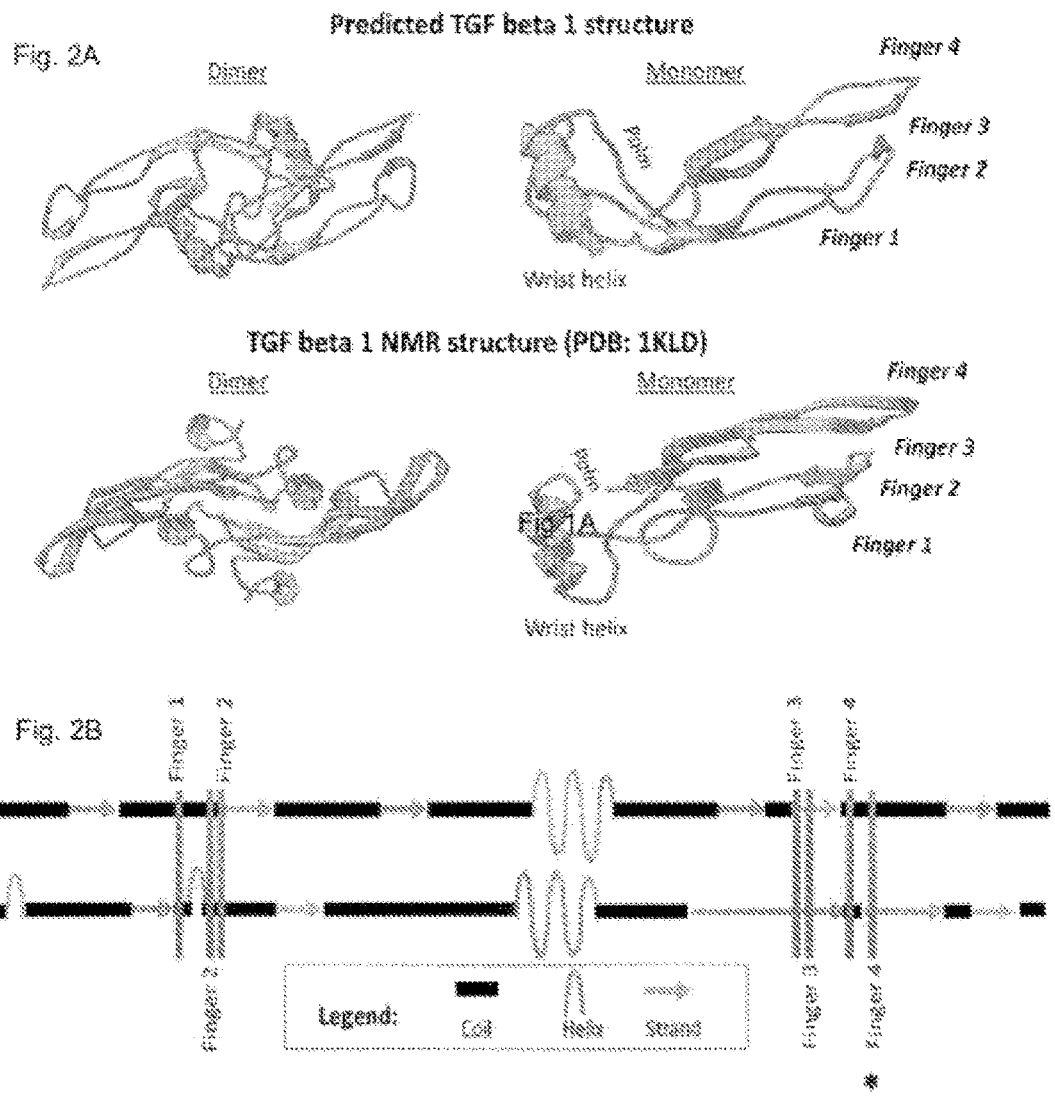
Figure 2. TGF-B1 domain mapping and configuration comparison of predicted with known structure using Phyre2 prediction tool. A) Predicted TGF-B1 structure and elucidated NMR structure of TGF-B1 dimer and monomer. B) Secondary structure comparison of the fingertip domains of TGF-B1 (SEQ ID NO:2).

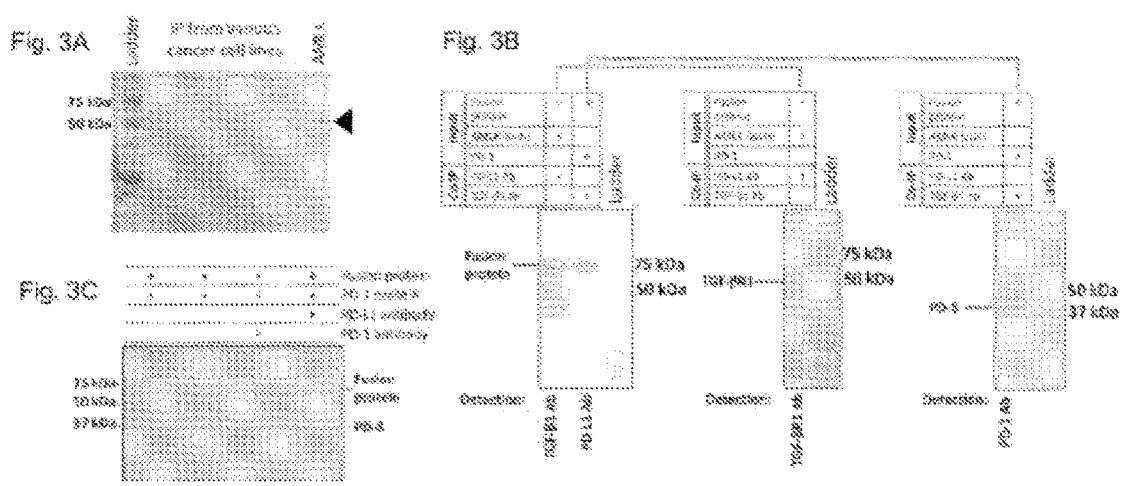
Figure 3. Binding analysis of fusion protein domains, TGF- B1 (SEQ ID NO: 2) and PD- L1 (SEQ ID NO: 6), with target receptors TGFB co-receptors and PD-1. A) Immunoprecipitation of TGFBR1. B) Western blot analysis of co-IP between fusion protein and their target receptors, TGFBRI and PD-1. C) SDS-PAGE profile of co-IP using fusion protein and PD-1.

Figure 4. Receptor binding of TGF-B1 domain of the fusion protein. A) Dot blot analysis following co-IP and reverse co-IP assays showing the absence of interaction between fusion protein and TGFBR1. B) ELISA assay to identify interaction between plate-coated TGFBR1 with TGF-B1 of the fusion protein. C) SDS-PAGE profile of co-IP experiment using AMLK cell lysate and fusion protein. D) Dot blot detection of TGFBR1 following co-IP. E) Schematic representation of chronologic order of TGF-B1 receptor binding.

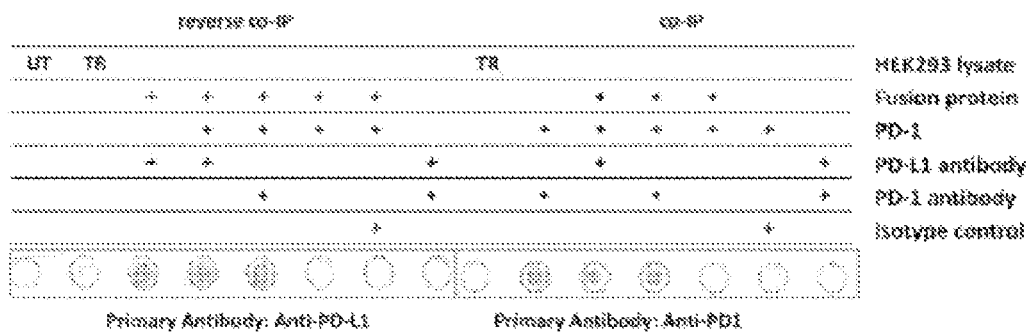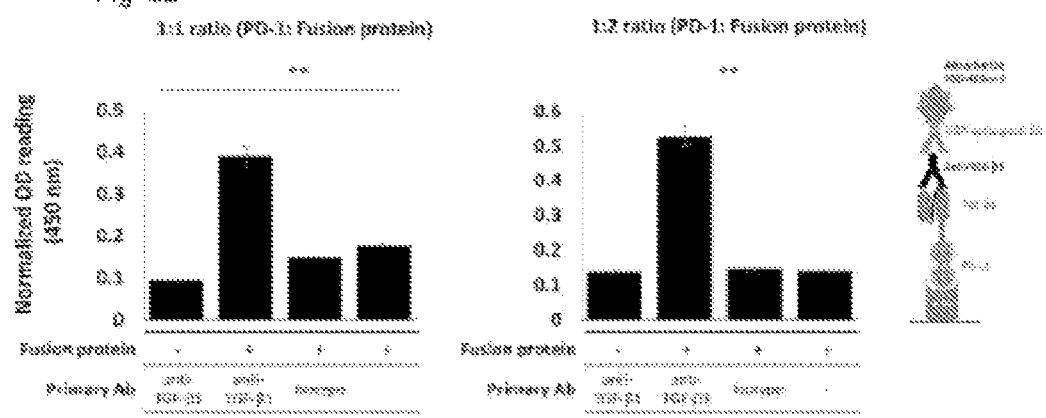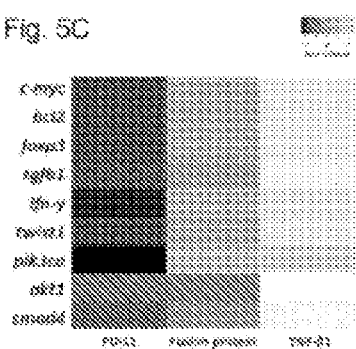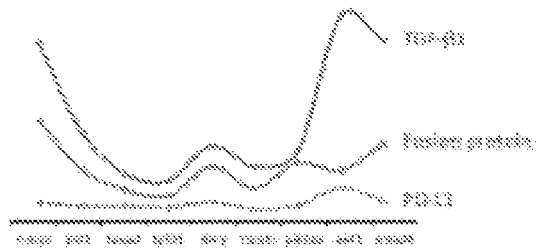
Figure 5. TGF-B1/PD-L1 Fusion protein (SEQ 10 NO: 13) bin

Fig.6A

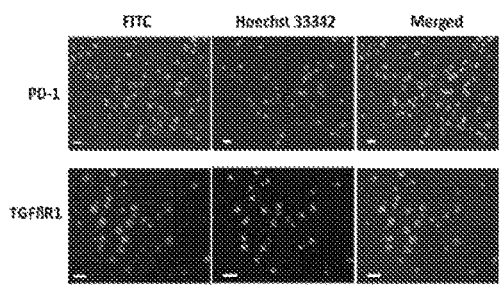

Fig.6B

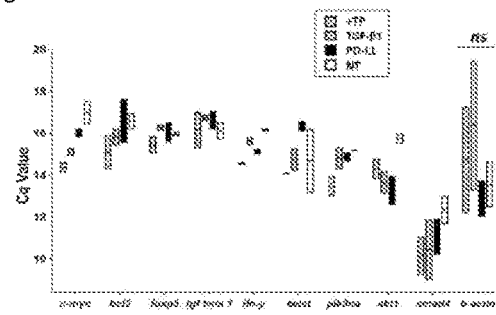

Figure 6. Receptor expression of fusion protein (SEQ 10 NO: 13) by AMLK and induction of gene expression by treatment of fusion protein (SEQ ID NO: 13), TGF-B1 (SEQ ID NO: 2), and PD-L1 (SEQ ID NO: 6). A) Immunofluorescence staining of AMLK cells visualizing the expression of both TGFBR1 and PD-1. B) Cq values of gene expression analysis by qRT-PCR of AMLK cells in response to treatment of fusion protein, TGF-B1, and PD-L1.

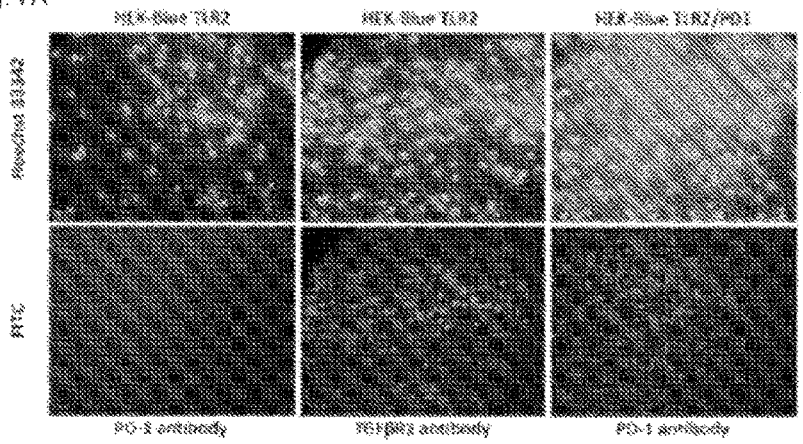
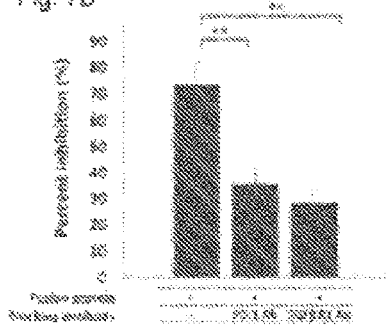
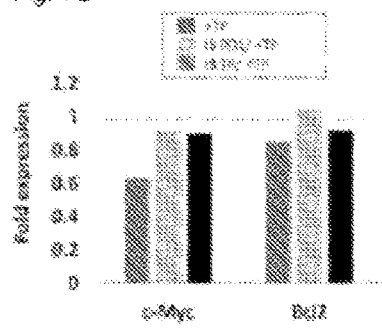
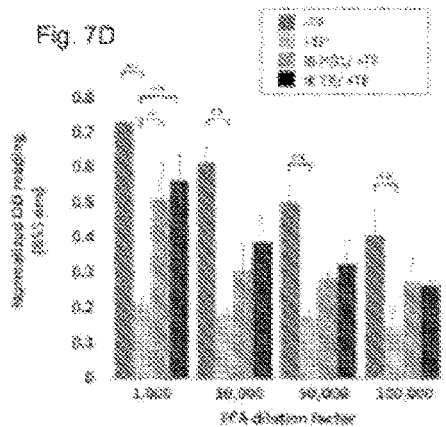
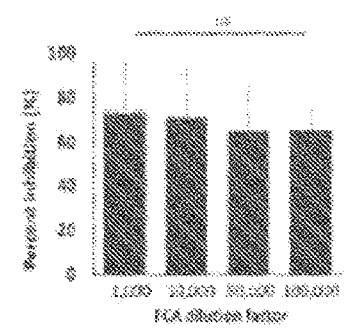
Figure 7. Concentration Dependent suppression of *NF-kB* activation by TGF-B1/PD-L1 fusion protein (SEQ ID NO:13).

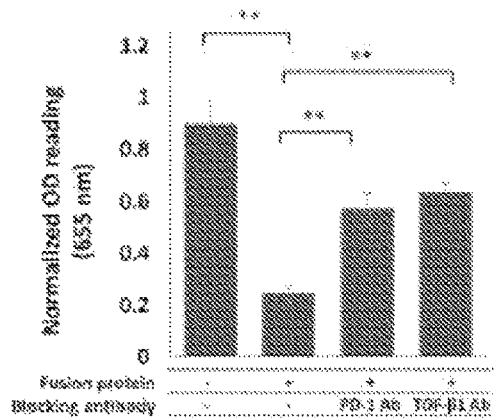
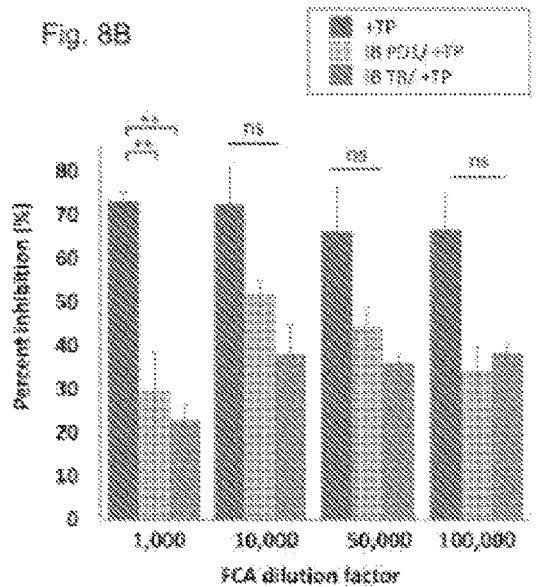
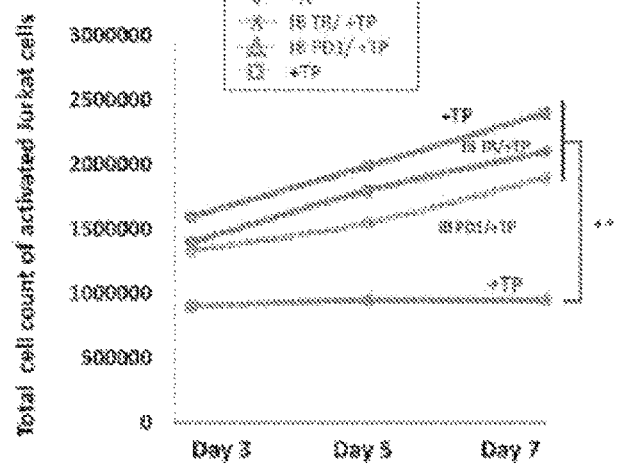
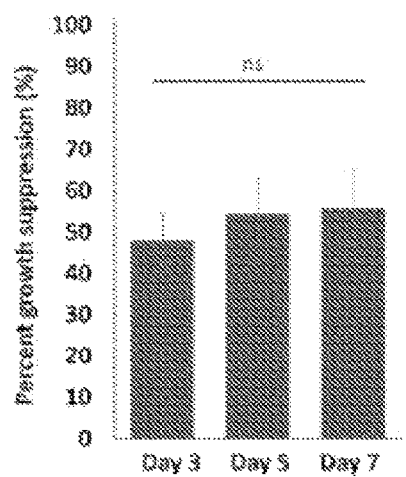

Figure 8. Immunosuppressive activity of the fusion protein (SEQ ID NO: 13) by inhibition of NFkB activation and suppression of activated effector-like cell growth. A) SEAP secretion by mycobacteria-challenged TLR-expressing HEK-Blue cells. B) Percent inhibition of SEAP secretion. C) Total cell count of PHA/IFN-g-activated Jurkat T cells. D) Percent growth suppression of activated Jurkat T cells.

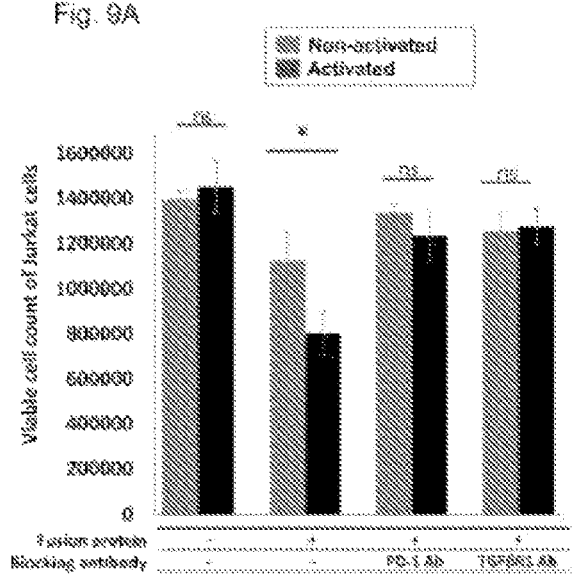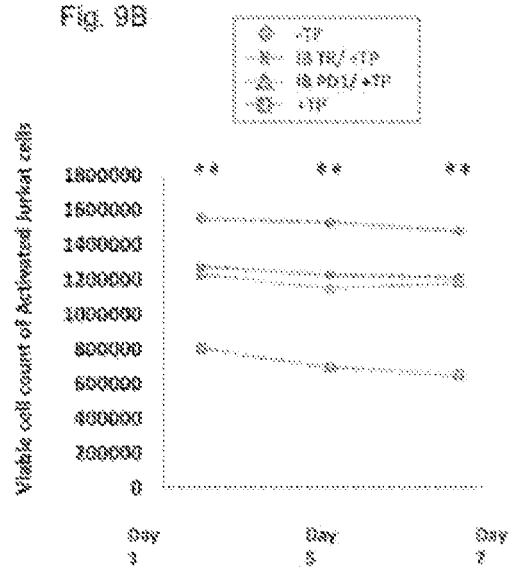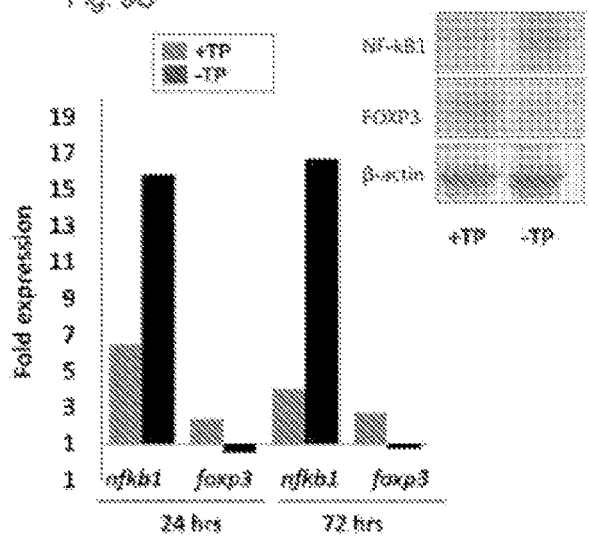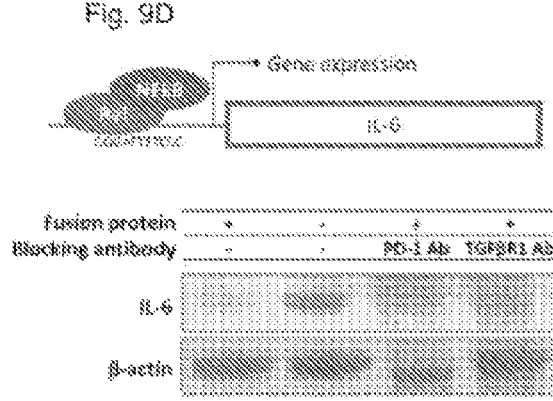

Figure 9. Downregulation of effector response by growth suppression and modulation of pro-inflammatory markers. A) Viable cell count of PHA/IFN-g activated and non-activated Jurkat T cells In response to treatment with fusion protein. B) Time--dependent growth suppression of activated Jurkat cells. C} Gene expression analysis of NFkB and FOXP3 in activated Jurkat cells. D) Western blot analysis of intracellular IL-6 in PHA/IFN-g activated Jurkat cells.

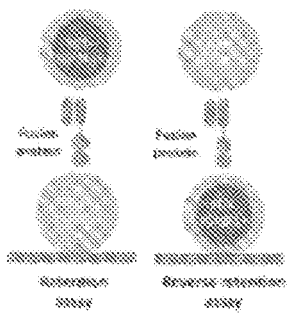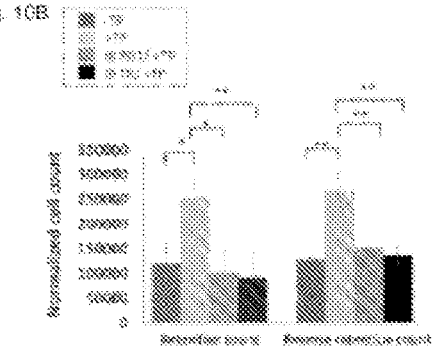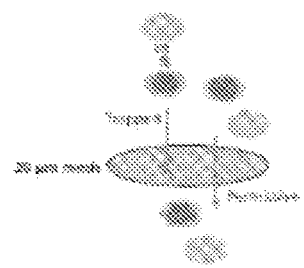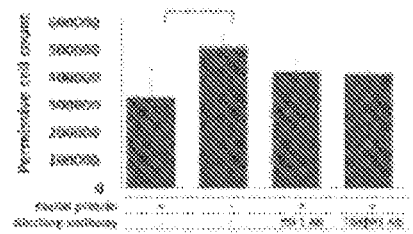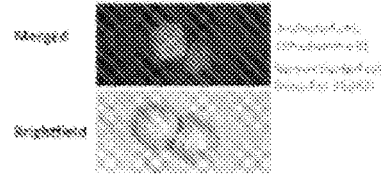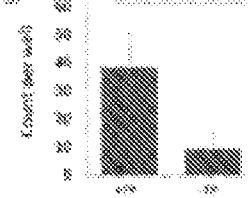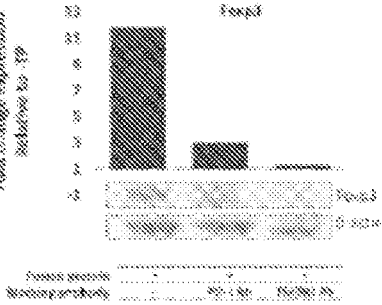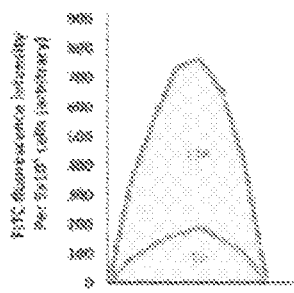
Figure 10. BiTE-like mechanism of TGF-BI/PD-L1 fusion protein (SEQ ID NO: 13).

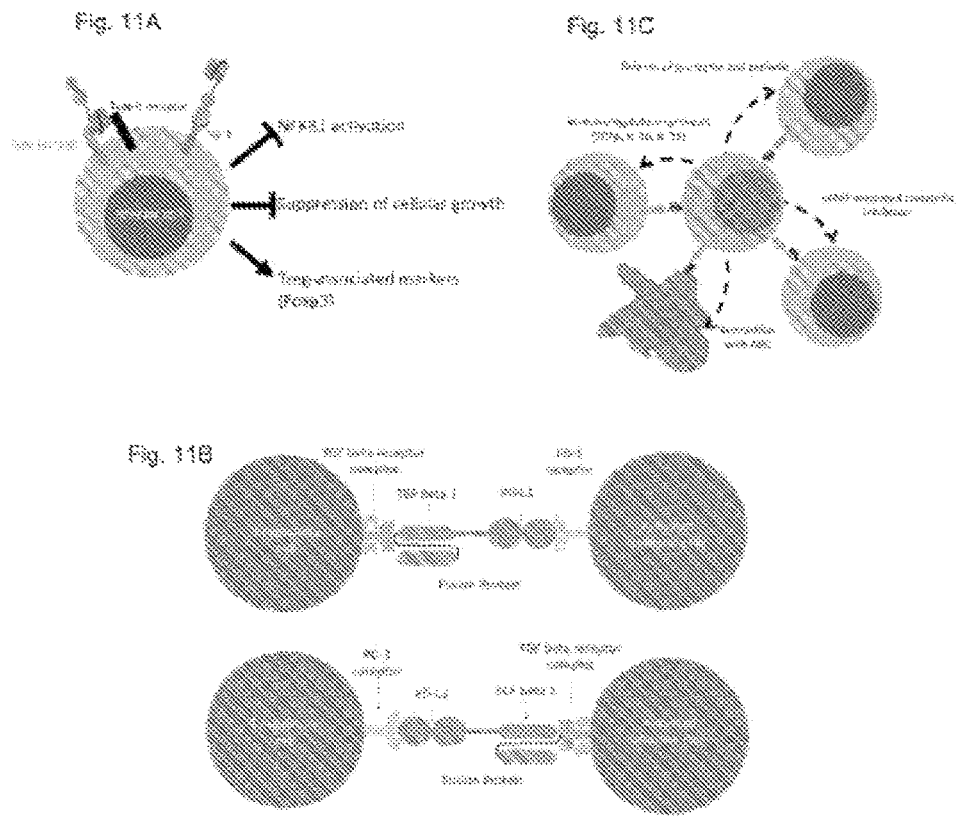

Figure 11. Proposed immunosuppressive mechanisms of the TGF-B1/PD-L1 fusion protein {SEQ ID NO: 13). A) Treg-independent control of effector functions by inhibition of NFkB activation, suppression of cell growth and upregulation of Treg-associated markers such as Foxp3. B) Proposed BiTE-like mechanism of the fusion protein to encourage Treg-mediated contact-dependent immune regulation. C} Molecular mechanisms of immunosuppression by Tregs potentially enhanced by the TGF-B1/PD-L1 fusion protein.

TGF-B1
dimer

ATGGCCCTGGACACCAACTATTGCTTCAGCTCCACGGAGAAGAACTGCTGCG
TGCGGCAGCTGTACATTGACTTCCGCAAGGACCTCGGCTGGAAGTGGATCC
ACGAGCCCAAGGGCTACCATGCCAACTTCTGCCTCGGGCCCTGCCCCTACAT
TTGGAGCCTGGACACGCAGTACAGCAAGGTCCTGGCCCTGTACAACCAGCA
TAACCCGGGCGCCTCGGCGGCGCCGTGCTGCGTGCCGCAGGCGCTGGAGCC
GCTGCCCATCGTGTACTACGTGGGCCGCAAGCCCAAGGTGGAGCAGCTGTC
CAACATGATCGTGCGCTCCTGCAAGTGCAGC*GGTGGAGGCGGTAGCGGTGG*

Flexible
linker

*AGGCGGTAGCGGTGGAGGCGGTAGC*ATGGCCCTGGACACCAACTATTGCTT
*CAGCTCCACGGAGAAGAACTGCTGCGTGCGGCAGCTGTACATTGACTTCCGC*
*AAGGACCTCGGCTGGAAGTGGATCCACGAGCCCAAGGGCTACCATGCCAAC*
*TTCTGCCTCGGGCCCTGCCCCTACATTTGGAGCCTGGACACGCAGTACAGCA*
*AGGTCCTGGCCCTGTACAACCAGCATAACCCGGGCGCCTCGGCGGCGCCGTG*
*CTGCGTGCCGCAGGCGCTGGAGCCGCTGCCCATCGTGTACTACGTGGGCCG*
*CAAGCCCAAGGTGGAGCAGCTGTCCAACATGATCGTGCGCTCCTGCAAGTGC*

Rigid
Spacer

AGCGCGGAAGCGGCGGCGAAAGAAGCGGCGGCGAAAGCG*TTTACTGTCAC*
*GGTTCC*CAAGGACCTATATGTGGTAGAGTATGGTAGCAATATGACAATTGA
ATGCAAATTCCCAGTAGAAAAACAATTAGACCTGGCTGCACTAATTGTCTAT
TGGGAAATGGAGGATAAGAACATTATTCAATTTGTGCATGGAGAGGAAGA
CCTGAAGGTTCAGCATAGTAGCTACAGACAGAGGGCCCGGCTGTTGAAGGA
CCAGCTCTCCCTGGGAAATGCTGCACTTCAGATCACAGATGTGAAATTGCAG

PD-L1

GATGCAGGGGTGTACCGCTGCATGATCAGCTATGGTGGTGCCGACTACAAG
CGAATTACTGTGAAAGTCAATGCCCCATACAACAAAATCAACCAAAGAATTT
TGGTTGTGGATCCAGTCACCTCTGAACATGAACTGACATGTCAGGCTGAGG
GCTACCCCAAGGCCGAAGTCATCTGGACAAGCAGTGACCATCAAGTCCTGA
GTGGTAAGACCACCACCACCAATTCCAAGAGAGAGGAGAAGCTTTTCAATG
TGACCAGCACACTGAGAATCAACACAACAACTAATGAGATTTTCTACTGCAC
TTTTAGGAGATTAGATCCTGAGGAAAACCATACAGCTGAATTGGTCATCCCA
GAACTACCTCTGGCACATCCTCCAAATGAAAGGTGA

Figure 12. DNA Sequence of TGF-B1/PD-L1 Fusion Gene (SEQ ID NO:1)

BI-FUNCTIONAL FUSION PROTEINS COMPRISED OF TGF-B AND IMMUNE CHECKPOINT DOMAINS

STATEMENT REGARDING FEDERALLY SPONSORED RESEARCH OR DEVELOPMENT

The subject matter of this patent application was not supported by U.S. Federal, U.S. State, Philippine Government, or any other Government-sponsored research or development program.

REFERENCE TO COMPACT DISC APPENDIX

None. The nucleotide and amino acid sequences are submitted as ASCII text file via EFS-Web.

BACKGROUND OF THE INVENTION

Traditionally, immunosuppressive drugs constitute the first-line therapy for many types of immune disorders, immune dysregulation, and autoimmune diseases (AID) [1]. Although these drugs help diminish disease pathology, they are associated with severe toxicity and are associated with a high risk of opportunistic infections [2-3] and other life-threatening complications among patients [4-6]. The introduction of targeted-based therapies has advanced the treatment of immune disorders and AID [7,8] and targeted-based biological agents such as infliximab [9] have recently become the interest for standard treatments, particularly in cases where first-line therapies fail to manage the disease [10-11].

Some potential ways to regulate the immune response are the TGF-B proteins. TGF-B proteins belong to the transforming growth factor family that includes three mammalian isoforms—TGF-B1, TGF-B2, and TGF-B3 that are produced by white blood cell lineages and are involved in modulating immune response and in maintaining immune tolerance [12-14]. TGF-B isoforms are pleiotropic cytokines that control various physiological processes such as cell growth, cell proliferation, cell differentiation, and morphogenesis [15-17], but the immune-specific regulatory effects of TGF-B proteins in various effector cells and how they act in concert with other cytokines still need to be elucidated [13,18-23].

Immune checkpoints are regulators of the immune system which are critical for self-tolerance, thereby preventing the indiscriminate attack of cells by the immune system [24]. Among the best known immune checkpoint is PD1 (Programmed Death 1) which has two ligands, Programmed Death Ligand—PD-L1 and PD-L2. These PD-L immune-regulatory ligands play important roles in maintaining peripheral tolerance by downregulating immune effector functions through binding with PD-1 receptors expressed by various cells of the innate and adaptive immune systems [24-26]. Defective PD-1/PD-L pathways correlate with the occurrence of various types of immune disorders, immune dysregulation, and autoimmune diseases [27]. Understanding the molecular biology of PD-L ligands has only recently developed, including studies of PD-1-deficient mice which were found to negatively regulate effector T cell functions and developed autoimmune symptoms [28]. The immune regulating activity of the PD-1/PD-L pathways has been shown in clinical settings for cancer immunotherapy utilizing antibodies that block the binding of these proteins to enhance immune response [29-30]. Another important checkpoint with clinical importance is CTLA-4 (Cytotoxic T-Lymphocyte-Associated protein 4) also called CD152, which binds to 2 distinct ligands, CD80 and CD86, leading to their removal from opposing cells; CTLA-4 acts as an immune regulatory mechanism by directly reducing the ability of APC to stimulate via CD28 and the activity of CTLA-4 on Treg cells serves to control T cell proliferation [31].

Recently, bispecific T cell engager (BiTE) technology has emerged as a new class of immunotherapy for cancer by increasing immune reactions targeted to tumor associated antigens [32]. This involves mainly the fusion of two scFvs (single-chain variable fragments) that recognize T cell marker and cancer antigen, allowing the recognition of cancer by cytotoxic T cells; this BiTE– mediated cell-to-cell contact may be an important mechanism to elicit regulatory T cell-mediated contact-dependent immune regulation. Various molecular mechanisms of immune regulation mediated by cell-to-cell contact were previously described [33] and appear to play important roles in the tolerogenic property of regulatory T cells with consequences in immune therapies of cancer [34]. Fusion proteins that incorporate antibody domains including anti-PDL1, anti TGF-beta receptor II, anti-TGF-beta, have been developed to enhance anti-cancer immunotherapy [35-37].

In contrast to the previously described BiTE technologies for cancer immunotherapy that use antibody domains, we now describe In this invention a different action and use of a new type of fusion protein that can play an important role in modulating immune responses in immune disorders and autoimmune diseases. We disclose the characterization of the biological activities of a novel bifunctional T regulatory cell engaging TGF-B/immune checkpoint fusion protein, using as proof of concept a TGF-B1/PD-L1 pair. When we created a new gene and protein fusion of these two ligands, we found that they worked in concert in a BiTE-like mechanism to favor Treg-mediated contact-dependent immune regulation. A dimeric form of TGF-B was constructed, linked by a flexible linker. We found that this fusion protein bound receptors of TGF-B1 and PD-L1 that are expressed by both regulatory and effector cells and opens up opportunities for controlling immune responses. The potential for further development as immune regulatory therapy was evaluated by assessing the downregulation pattern of NF-kB1 activation including its target genes, its ability to suppress the growth of activated effector-like Jurkat cell, and the subsequent analysis of expression patterns of inflammatory and regulatory-associated markers. The BiTE mechanisms were evaluated further by measuring the frequency of cell-to-cell contact. Our data demonstrate the potential applications of TGF-B/immune checkpoint bifunctional fusion proteins with anti-inflammatory activity that represent a new class of therapy for Immune disorders, immune dysregulation, and autoimmune diseases. As proof of concept, a TGF-B1/PD-L1 fusion pair was used to demonstrate the immune regulatory activity of the fusion protein.

Keywords:
TGF-beta; Immune checkpoint; PD-L1; fusion protein; T regulatory cells; Immune disorders, immune dysregulation, autoimmune diseases

BRIEF SUMMARY OF THE INVENTION

Molecular crosstalk between effector immune cells and inhibitory cytokines as well as interactions with regulatory cells are mechanisms by which the immune response is regulated and controlled [7-8]. In immune disorders, immune dysregulation, and autoimmune diseases (AID), the failure of these regulatory checkpoints against autoreactive immune cells characterize the pathogenesis and progression of the disease. This invention describes the construction of TGF-B/immune checkpoint proteins, tested using a TGF-B1/PD-L1 fusion pair, that act in concert to maintain tolerance for self-antigens by stimulating regulatory cells and to regulate the activities of effector cells. The binding activity and bioactivity of this bifunctional TGF-B1/PD-L1 fusion protein were characterized with emphasis on assessing its therapeutic potential for treatment of immune disorders and autoimmune diseases. The functional components of the fusion protein comprising a TGF-B1 ligand in dimeric form and a PD-L1 domain functionally bind their respective receptors, inhibit NF-kB activation in Secreted Embryonic Alkaline Phosphatase (SEAP) reporter assays, and collaborate to downregulate NF-kB-responsive genes. The fusion protein selectively suppressed the growth of PHA/IFN-γ-activated effector-like Jurkat T cells with subsequent upregulation of Foxp3 and downregulation of NF-kB1 and IL-6. The receptor expression of these ligands suggests their utilization as bispecific T cell engager (BiTE) for Treg-mediated contact-dependent immune regulation. We also demonstrated that our fusion protein elicited a high frequency of cell-to-cell contact that induced upregulation of Treg-associated markers (Foxp3 and IL2RA) in a cellular co-culture set-up. These findings lend support for the concept of redirecting BiTE technology to treat immune disorders, immune dysregulation, and autoimmune diseases. By combining the activity of these two ligands, this fusion of TGF-B and immune checkpoint protein acts to modulate inflammatory signals and represents a new class of therapy for autoimmunity. As proof of concept, we used a TGF-B1/PD-L1 fusion pair.

Purpose of Invention:

To develop bifunctional T regulatory engaging fusion genes and proteins using a TGF-B domain in dimeric form consisting of TGF-B1 and as fusion pair, a domain consisting of PD-L1, that has applications for immune modulation and therapy for immune disorders, immune dysregulation, and autoimmune diseases.

Description of Problem(s) that this Invention Solves:

Immune disorders, immune dysregulation, and autoimmune diseases are conditions that are very complex and highly heterogeneous, presenting major challenges to clinical management. There are more than 80 clinical subtypes of immune diseases and current immunotherapies are only implicated for certain types. Overall, there are very few immunotherapies available for autoimmune diseases.

The technology described in this invention of a TGF-B domain fused with an immune checkpoint domain provides a unique solution that could help alleviate the shortage of therapies available for immune disorders, immune dysregulation, and autoimmune diseases.

Description—how the Invention is an Improvement Over Existing Technology:

This invention is an improvement over the existing technology in the creation/construction of a bifunctional protein with a TGF-B domain fused with an immune checkpoint domain, demonstrated by a TGF-B1/PD-L1 fusion protein that presents a more specific, more effective, and less toxic form of immunotherapy compared to the existing treatments available for: a) patients with immune disorders, immune dysregulation, and autoimmune diseases, b) patients who are unable to tolerate toxicities of existing immune therapies, c) patients who have developed resistance to current immune therapies, and d) patients who suffer from toxic side-effects of immune therapies.

Individuals and Business Demographics that would Use this Invention:

There are several potential applications for the immune-regulatory activity of this novel TGF-B/Immune checkpoint fusion gene and protein, including treatment for:

1. patients with autoimmune diseases,
2. patients with immune dysregulation conditions,
3. patients who are unable to tolerate toxicities of existing immune therapies
4. patients who develop resistance to existing immune therapies
5. patients who develop toxicity from immune reactions as a result of immunotherapies with immune checkpoint inhibitors, including, but not limited to, anti-PDL1, anti-PD1, anti-CTLA-4, and other immune checkpoint inhibitors.
6. patients who develop toxicity from immune disorders, immune reactions, and immune dysregulation, inflammatory reactions, cytokine release syndromes, as a result of Chimeric Antigen Receptor T (CAR-T) cell treatments, other treatments with adoptive T Cells, Natural Killer (NK) Cells and Natural Killer T (NKT) Cells, Cytokine Induced Killer (CIK) Cells, Dendritic Cells, Tumor-Infiltrating Lymphocytes (TIL) and other immune-stimulating cellular treatments.
7. patients who develop immune disorders, immune reactions, immune dysregulation, inflammatory reactions, cytokine release syndromes from infectious illnesses such as COVID-19, other coronoviruses, influenza, other viral illnesses, bacterial, fungal and parasitic diseases, including syndromes associated with sepsis.

Description of the Benefits of this Invention to its Users:

This invention offers to its users a new form of immune therapy with greater efficacy, less toxicity, and greater affordability in the long term management of patients.

BRIEF DESCRIPTION OF THE DRAWINGS

The Applicant has attached the following illustrations of the aforementioned invention:

FIG. 1. Development of a novel TGF-B1/PD-L1 fusion protein.

A) Schematic representation of fusion gene construct expressed under the control of a CMV promoter. TGF-B1 (SEQ ID NO: 2) was dimerized into TGF-B1 dimer (SEQ ID NO: 21) by fusing two monomers with a flexible peptide linker (GGGGS)3 (SEQ ID NO: 20) and fused with the PD-L1 extracellular domain (SEQ ID NO: 6) using a rigid peptide linker A(EAAAK)2A (SEQ ID NO: 27). B) SDS-PAGE profile of HEK 293 cells transfected with pCDNA3.1+/TP (containing the fusion gene) or pCDNA3.1+ only (empty control vector) following 48 hrs of lipofection. Black arrow indicates expected molecular size of the fusion product (~70 kDa). C) Immunoprecipitation (IP) of fusion protein using magnetic beads coupled with either anti-PD-L1 or anti-TGF-B1 antibodies. D) Molecular weight comparison between the fusion protein immunoprecipitated with either anti-PD-L1 or anti-TGF-B1 antibodies and mammalian-derived full-length PD-L1 protein using SDS-PAGE. E) Schematic representation of the TGF-B1/PD-L1 fusion protein (SEQ ID NO: 13).

FIG. 2. TGF beta 1 domain mapping and configuration comparison of predicted with known structure using Phyre2 prediction tool.

A) Predicted TGF-B1 structure (upper) and elucidated NMR solution structure of TGF-B1 (PDB ID: 1KLD) (lower) showing the dimer form (SEQ ID NO: 21) on the left and the monomeric form (SEQ ID NO: 2) on the right. B) Secondary structure comparison of the fingertip domains of TGF—B1 (SEQ ID NO: 2) which are involved in receptor binding. All structures were predicted to be the same in both except residue 97 (marked with *) in Finger 4.

FIG. 3. Binding analysis of fusion protein domains, TGF-B1 (SEQ ID NO: 2) and PD-L1 (SEQ ID NO: 6), with target receptors TGFB receptors and PD-1.

A) Immunoprecipitation of TGFBR1 from cancer cell lines using anti-TGFBR1-coupled magnetic beads. AMLK cells yielded presence of band at the desired molecular weight of 53 kDa which coincide with the size of TGFBR1. B) Western blot analysis of co-IP between fusion protein and their target receptors, TGFBR1 and PD-1. Presence of signal in the desired molecular sizes (70 kDa for fusion protein, 53 kDa for TGFBR1 and 45 kDa for PD-1) suggested the interaction of fusion protein domains with their physiological receptors. C) SDS-PAGE profile of co-IP using fusion protein and PD-1, presence of bands corresponding to sizes of both proteins indicated presence of interaction.

FIG. 4. Receptor binding of TGF-B1 (SEQ ID NO: 2) domain of the fusion protein (SEQ ID NO: 13).

A) Dot blot analysis following co-IP and reverse co-IP assays showing the absence of interaction between fusion protein and TGFBR1 (TR=pCDNA3.1+/TP-transfected cells; UT=untransfected). Co—IP with anti-TGF-B1-coupled magnetic beads failed to produce signal of TGFBR1 which is consistent with the use of anti-TGFBR1-coupled beads. B) Normalized OD450 nm reading in capture ELISA to identify interaction between plate-coated TGFBR1 with TGF-B1 of the fusion protein. Data are presented as mean value from plate readings of six wells and error bars represent+/−SD. Statistical analysis using one-way analysis of variance (ANOVA) revealed no statistical differences (ns) among the set-ups. C) SDS-PAGE profile of co-IP experiment using AMLK cell lysate and fusion protein. Three potential co-receptors bind TGF-B1 with molecular sizes of 53 kDa, 120 kDa, >250 kDa. D) Dot blot detection of TGFBR1 following co-IP in FIG. 4C showing the presence of signal between TGF-B1 and TGFBR1, suggesting the requirement of co-receptor for TGFBR1 binding. F) Schematic representation of chronologic order of TGF-B1 receptor binding.

FIG. 5. The TGF-B1/PD-L1 fusion protein (SEQ ID NO: 13) binds PD1 receptor and elicits gene expression signature similar to endogenous forms.

A) Dot blot analysis following co-IP and reverse co-IP assays showing the presence of interaction between fusion protein and PD-1 (TR=pCDNA3.1+/TP-transfected cells; UT=untransfected). Co—IP with anti-PD-L1-coupled magnetic beads resulted in the detection of PD-1 signal which is consistent with the use of anti-PD-1-coupled beads. B) Capture ELISA assay where PD1 was coated on the substrate allowing the binding with PD-L1 domain of fusion protein. Detection proceeded by probing the TGF-B1 domain of the fusion protein with anti-TGF-B1 antibody. Data are presented as mean value from plate readings of six wells and error bars represent +/−SD. Significance was determined by one-way analysis of variance (ANOVA). **p-value<0.01. C) Heat map signature of fold change expression of TGF-B1 and PD-L1-target genes in AMLK by treatment of cells with 50 ng/mL of PD-L1 (SEQ ID NO: 6), TGF-B1 (SEQ ID NO: 2), and fusion protein (SEQ ID NO: 13) for 36 hrs. D) Line plot of gene expression profile in C capturing the combinatorial expression values of genes from TGF-B1 (SEQ ID NO: 2), and PD-L1 (SEQ ID NO: 6), by the fusion protein (SEQ ID NO: 13), suggesting the functional activation of both signaling in fusion protein.

FIG. 6. Receptor expression of the fusion protein (SEQ ID NO: 13) by AMLK and induction of gene expression by treatment of fusion protein (SEQ ID NO: 13), TGFB-1 (SEQ ID NO: 2), and PD-L1 (SEQ ID NO: 6).

A) Immunofluorescence staining of AMLK cells visualizing the expression of both TGFBR1 and PD-1. B) Cq values of gene expression analysis by qRT-PCR in response to treatment of fusion protein, TGFB-1 and PD-L1 by AMLK cells. Beta actin expression was used as control. Experiment was performed in duplicate. Statistical analysis was performed using Analysis of Variance (ANOVA). ns=not significant.

FIG. 7. Concentration-dependent suppression of NF-κB activation by TGF-B1/PD-L1 fusion protein (SEQ ID NO: 13).

A) Immunofluorescence staining of TGFBR1+PD-1+TLR2-expressing HEK293 cells with endogenous expression of TGFBR1 and a transgenic expression of a full-length human PD1 protein. TLR2 pathway induces NF-kB-mediated secretion of embryonic alkaline phosphatase (SEAP) which served as reported of NF-kB activation in response to challenge with mycobacteria-containing Freund's complete adjuvant (FCA). B) Percent inhibition of SEAP secretion by transgenic TLR2-expressing HEK293 cells treated with 1:100 dilution of FCA after 24 hrs. Fusion protein treated samples were normalized over treatment without fusion protein as mentioned in materials and methods section. Pre-incubation of cells with blocking antibodies specific to receptor targets (PD-1 Ab and TGFBR1 Ab) of fusion proteins served to assess receptor-ligand specificity of SEAP readings. C) Fold-change expression of NF-kB-target genes, c-myc and bcl2 in the presence of fusion protein or pretreatment of receptor blocking antibodies. Broken line represents comparative expression of untreated set-up. +TP=with fusion protein; IB PD1/+TP=with anti-PD-1 blocking; IB TR/+TP=with anti-TGFBR1 blocking. Expression values were derived from Cq values obtained in duplicates. D) Normalized raw optical density reading (655 nm) of SEAP secretion in higher FCA dilutions (1:1000, 10000, 50000, 100000). +TP=with fusion protein; −TP=without fusion protein; IB PD1/+TP=with anti-PD-1 blocking; IB TR/+TP=with anti-TGFBR1 blocking. E) Percent inhibition of SEAP secretion in higher dilutions. All data are presented as mean value (D) or percentage as derived from the formula indicated in materials and method section (B, E) from plate readings of eight wells and error bars represent+/−SD. Multiple comparison of significance was determined by Tukey's HSD test. *p-value<0.05; **p-value<0.01; ns=not significant.

FIG. 8. Immunosuppressive activity of the fusion protein (SEQ ID NO: 13) by inhibition NF-kB activation and suppression of activated effector-like cell growth.

A) Normalized OD655 nm reading of SEAP secretion by mycobacteria-challenged TLR-expressing HEK-Blue cells using 1:100 dilution of FCA after 24 hrs. Pre-incubation of cells with blocking antibodies specific to receptor targets (PD-1 Ab and TGFBR1 Ab) of fusion proteins served to assess receptor-ligand specificity of SEAP readings. B) Percent inhibition of SEAP secretion in higher dilutions (1:1000, 1:10000, 1:50000, 1:100,000). C) Total cell count of PHA/IFN-γ-activated Jurkat cells following cultures after 3, 5 and 7 days. Cell count was assayed using trypan blue staining. D) Percent growth suppression of activated Jurkat T cells derived from viable cell count data in FIG. 5B, showing 45-55% percent suppression by the fusion protein with 1 week of culture. All data are presented as mean value (A, C) or percentage derived from the formula indicated in materials and method section (B, D) from plate readings of eight wells (A,B) or three independent replicates (C,D) and error bars represent+/−SD. Multiple comparison of significance was determined by Tukey's HSD test. *p-value<0.05; **p-value<0.01; ns=not significant.

FIG. 9. Downregulation of effector response by growth suppression and modulation of proinflammatory markers.

A) Viable cell count of PHA/IFN-γ activated and non-activated Jurkat T cells in response to treatment with fusion protein assayed using trypan blue staining. Cells treated with receptor-specific antibodies PD-1 Ab or TGFBR1 Ab served as activity controls. B) Time-dependent growth suppression of activated Jurkat cells after 3, 5 and 7 days of culture. Data (in A and B) are presented as mean value of three independent experiment and error bars represent+/−SD. Significance was determined by two-tailed unpaired Student's t-tests. *p-value<0.05; **B<0.01; ns=not significant. C) Gene expression analysis of nfkb1 and foxp3 in activated Jurkat cells cultured in the presence (+TP) or absence (−TP) of fusion protein (SEQ ID NO: 13) after 24 and 72 hrs. Horizontal axis was set to 1 (normalized to non-activated cells). All data >1 was considered upregulated while <1 was considered down regulated. RNA expression was validated using westernblot analysis utilizing lysates of cells treated after 72 hrs. B-actin served as loading control. D) Westernblot analysis of intracellular IL-6 in PHA/IFN-γ activated Jurkat cells after 72 hrs of culture. B-actin served as loading control.

FIG. 10. BiTE-like mechanism of TGF-B1/PD-L1 fusion protein (SEQ ID NO: 13) to elicit Treg-mediated contact-dependent immune control.

A) Cellular retention assay to measure frequency of cell-to-cell contact. Target cells were coated on a poly-L-lysine-coated substrate and were treated with or without the fusion protein. Binding cells were added in 1:1 (target: binding) ratio followed by gentle washing. Total cell count was determined, and bona fide cellular retention count was derived by normalizing the cells with a "no binding cell" set-up. B) Normalized retention count. Data are presented as mean value from plate counts in eight wells and error bars represent+/−SD. Multiple comparison of significance was determined by Tukey's HSD test. *p-value<0.05; p-value<0.01. C) Size exclusion assay similar in FIG. 10**A, except cells were premixed already and no substrate attachment of cells. The 20 μm mesh strainer trapped cells that are clumped together. Low cell count indicates high frequency of clumping and the use of receptor blocking controls served as specificity control. D) Cell count of cells that passed through the 20 μm mesh. Data are presented as mean value of four independent replicates and error bars represent+/−SD. Multiple comparison of significance was determined by Tukey's HSD test. *p-value<0.05; p-value<0.01. E) Assessment of cell-to-cell contact by the fusion protein in Jurkat cells. PHA/IFN-γ-activated ells were pre-stained with Rhodamine B and Hoechst 33342-labelled non-activated Jurkat cells. F) Frequency of Rhodamine B-Hoechst 33342 co-localized (paired) cells. Data are presented as mean value of three independent replicates and error bars represent+/− SD. Significance was determined by two-tailed unpaired Student's t-test. p-value<0.01. G) Foxp3 expression in co-culture of PHA/IFN-γ activated and non-activated Jurkat T cells after 24 hrs. Horizontal axis was set to 1 (normalized to non-activated cells). All data >1 was considered upregulated while <1 was considered down regulated. Protein level was assessed using westernblot utilizing B-actin as loading control. H) PHA/IFN-γ activated and non-activated Jurkat T cells are stained with FITC-conjugated anti-CD25 antibody after 3 days of co-culture. FITC fluorescence intensity of 5×105 cells using fluorometer (ex430-495 nm/em510-580 nm). Data from six replicates were plotted and represented using a shaded histogram. +TP=co-culture with fusion protein; −TP=without fusion protein.

FIG. 11. Immunosuppressive mechanisms of the TGF-B1/PD-L1 fusion protein (SEQ ID NO: 13).

A) Treg-independent control of effector functions by inhibition of NF-kB activation, suppression of cell growth and upregulation of Treg-associated markers such as Foxp3. These mechanisms are well-studied physiological consequences of signaling pathway elicited by both TGF-B1 and PD-L1.

B) Proposed BiTE-like mechanism of the fusion protein (SEQ ID NO: 13) to encourage Treg-mediated contact-dependent immune regulation. C) Molecular mechanisms of immunosuppression by Tregs which could potentially be enhanced by the fusion protein FIG. 12: DNA Sequence of the TGF-B1/PD-L1 Fusion Gene (SEQ ID NO:1).

Table 1. Primer pairs used in gene expression analysis. Sequence ID No is indicated for each primer sequence.

Table 2. Fold change expression of immune related genes in AMLK cells treated with treated with fusion protein (SEQ ID NO: 13), TGF-B1(SEQ ID NO: 2) and PD-L1 (SEQ ID NO: 6).

1.0 Description of the Binding Activity and Functions of the Domains of the Fusion Protein:

This invention presents a description of a bifunctional gene and protein with a TGF-B domain fused with an immune checkpoint domain, demonstrated by a novel TGF-B1/PD-L1 fusion protein (SEQ ID NO: 13), the characterization of its bioactivity, and exploitation of its therapeutic potential for autoimmunity. In this patent application, the proof of concept using a new combination of TGF-B1 (SEQ ID NO: 2) and PD-L1 ligands (SEQ ID NO: 6) in a fusion protein ID NO: 13), is designed to act in concert to maintain tolerance for self-antigens by stimulating regulatory cells and to regulate the activities of effector cells.

First, the TGF-B1 and PD-L1 domains were demonstrated to functionally bind their respective receptors and inhibit NF-kB activation in our SEAP reporter assay which collaborate with the downregulation of NF-kB-responsive genes.

Next, the fusion protein treatment was shown to selectively suppress the growth of PHA/IFN-γ-activated effector-like Jurkat T cells with subsequent upregulation of Foxp3 and downregulation of NF-kB1 and IL-6. The receptor expression of these ligands suggests their utilization as bispecific T cell engager (BiTE) for Treg-mediated contact-dependent immune regulation.

The fusion protein described herein elicited a high frequency of cell-to-cell contact and upregulated Treg-associated markers (Foxp3 and IL2RA) in a cellular co-culture set-up.

1.1 Description of the Parts and Components of the Fusion Protein:

The functional components of the fusion gene and protein are: (1) TGF-B ligand (SEQ ID NO: 2) which is important in maintaining tolerance for self-antigens by stimulating regulatory cells; (2) an immune checkpoint domain (PD-L1, SEQ ID NO: 6) that is a crucial gatekeeper in regulating the activities of effector cells; (3) a flexible peptide linker (SEQ ID NO: 20) used to link two TGF-B domains resulting in a dimeric TGF-B construct, wherein the flexible linker is preferred for a configuration of the dimeric form of the TGF-B ligand binding to the PD-1 receptor; and (4) a rigid peptide linker (SEQ ID NO: 27) for connecting the dimeric PDF-B ligand (SEQ ID NO: 21) to the immune checkpoint domain In detail, the components and characteristics of the fusion protein are:
- (i) a Transforming Growth Factor— Beta (TGF-B) ligand, consisting of TGF-B1 (SEQ ID NO: 2) and (ii) an immune checkpoint ligand, wherein the immune checkpoint ligand is PD-L1 (SEQ ID NO: 6), and wherein the TGF-B ligand and immune checkpoint ligands are capable of binding to TGF-B receptors and immune checkpoint receptors, respectively, that are expressed in human and animal cells.

(iii) a flexible peptide linker (SEQ ID NO: 20) that links two TGF-B domains resulting in a dimeric TGF-B construct wherein the dimeric form of the TGF-B ligand (SEQ ID NO: 21) is important for its binding and functional activity.

(iv) a rigid peptide linker (SEQ ID NO: 27), wherein the dimeric TGF-B ligand (SEQ ID NO: 21) is linked to the immune checkpoint ligand PD-L1 (SEQ ID NO: 6).

1.2 Relationship Between the Parts of the Invention:

Experiments with the TGF-B1/PD-L1 fusion protein (SEQ ID NO: 13) show that these two ligands work in concert to regulate immune reactions by: a) exploiting the ability of the TGF-B1 ligand to maintain tolerance for self-antigens by stimulating regulatory cells, and at the same time, b) exploiting the ability of the PD-L1 ligand to act as an immune gatekeeper in regulating the activities of effector cells.

1.3 Summary of Fusion Protein Binding Activity and Functions:

The TGF-B/Immune checkpoint fusion protein exemplified by TGF-B1/PD-L1 fusion protein (SEQ ID NO: 13) was comprised of TGF-B1 and PD-L1 domains that bound to their respective receptors, inhibited NF-kB activation, and collaborated to downregulate NF-kB-responsive genes. The TGF-B1/PD-L1 fusion protein selectively suppressed the growth of PHA/IFN-γ-activated effector-T cells to regulate immune reactions.

1.4 Unique Features of Invention:

This invention describes the construction of TGF-B/immune checkpoint bifunctional fusion gene and protein with anti-inflammatory activity that represents a new class of therapy for Immune disorders, immune dysregulation, and autoimmune diseases. As proof of concept, a TGF-B1/PD-L1 gene (SEQ ID NO: 1) and its corresponding amino acid sequence (SEQ ID NO: 13) fusion pair, were used.

This invention is unique in the engineering of a dimeric TGF-B1 (SEQ ID NO: 21), which was experimentally shown to be important in its binding and functional activity. This invention utilizes the ability of dimeric TGF-B to control effector cells while activating regulatory cells, controlling unwanted inflammation in autoimmunity, combined with the ability of the immune checkpoint domain to control other effector subsets including TH17 and TH9 which cannot be controlled by TGF-B1.

This invention is also unique in utilizing a flexible linker (SEQ ID NO: 20) to create the dimeric TGF-B1 (SEQ ID NO: 21), and in utilizing a rigid peptide linker (SEQ ID NO: 27) to link the dimeric TGF-B1 (SEQ ID NO: 21) to a PD-L1 domain (SEQ ID NO: 6).

This invention expands the therapeutic options for patients with immune disorders, immune dysregulation, and autoimmune diseases, especially those patients who have few other therapeutic options or who have developed resistance to current immune therapies.

2.0 Disclosure of Materials and Methods:

2.1. Cell Lines

AMLK cells and Jurkat T cells were maintained in RPMI-1640 (Gibco, Calif., USA) while HEK 293 cells and HEK-Blue TLR2-expressing cells (PlasmoTestTM, Invivogen, Calif., USA) were maintained in DMEM basal medium (Gibco, Calif., USA). All media were supplemented with 10% FBS (fetal bovine serum), 1 mM L-glutamine, 1 mM sodium pyruvate, 1.5 g/L sodium bicarbonate, 50 U/mL penicillin and 50 μg/mL streptomycin. Jurkat T cell activation and induction of PD1 expression were performed by adding 1 μg/mL of PHA or phytohemagglutinin (L1668, Sigma-Aldrich, MO, USA) and 0.1 μg/mL IFN-γ (SRP3058, Sigma-Aldrich, MO, USA) in the medium. All experiments with HEK-Blue TLR2-expressing cells were performed with the addition of 100 μg/mL NormocinTM (PlasmoTestTM, Invivogen, Calif., USA) to prevent *mycoplasma* contamination. Cells were cultured at 37° C. with 5% CO2.

2.2. Antibodies and Proteins

Active PD1 protein (ab214141), anti-PD-L1 (ab210931), anti-CD25 (ab9496) and FITC anti-mouse IgG (ab97022) were obtained from Abcam (CA, USA). PD-L1 (10084-HNAH) and TGF-beta 1 (10804-HNAC) proteins were purchased from Sino Biological Inc (Wayne, Pa., USA). Anti-TGFBR1 (sc518018), HRP-conjugated anti-murine IgGk (sc516102) were obtained from Santa Cruz Biotechnology (USA). Anti-TGF-B1 (525301), anti-PD-1 (367402), FITC anti-CD25 (356106), FITC anti-PD-1 (329904), anti-Foxp3 (320001), anti-B-actin (643801), anti-IL-6 and avidin-conjugated HRP (430504) were purchased from Biolegend (CA, USA). Anti-NF-KB1 (p105/p50, NBP2-22178) was obtained from Novus Biologicals.

2.3. Immunoprecipitation (IP)

TGFBR1 was isolated from AMLK cells using a modified protein extraction buffer using 100 mM EDTA instead of 2 μM TCEP. Purification of TGFBR1 was performed using DynabeadsTM M-280 (Invitrogen, USA) covalently coupled with anti-TGFBR1 following the manufacturer's suggested protocol. Magnetic separation was carried out using DYNAL® (Invitrogen, Calif., USA). Protein quantification was performed using a Qubit 2.0 protein assay (Invitrogen, Calif., USA). The same procedure was used to IP fusion protein using magnetic beads coupled with either anti-TGF-B1, anti-PD-1, or anti-PD-L1.

2.4. Co-Immunoprecipitation (Co-IP) and Reverse Co-IP

Each receptor targets (PD1 or TGFBR1) were combined separately with purified fusion protein in 1:1 ratio (for co-IP using AMLK lysate, a 2:1 lysate to fusion protein ratio was used) in a maximum of 50 μL PBS reaction volume, incubated for 15 mins at room temperature with gentle shaking. For co-IP, magnetic beads coupled with anti-PD-L1 or anti-TGF-B1 was used. For reverse co-IP, anti-PD1 or anti-TGFBR1 was used. Antibody-coupled beads were added in 25 μL volume. The reactions were incubated for 30 mins at room temperature with constant shaking. The tubes were placed on a magnetic rack and washing was performed using PBS three times and the protein complexes were eluted using 20 μL of 100 mM glycine-HCl (pH 3.0) for 1 min followed by neutralization using 2 μL of 1M Tris-HCl (pH 8.8). IgG kappa anti-CD25 antibody served as an isotype control.

2.5. SDS-PAGE Analysis

At least 1 μg of protein samples were mixed in a 1:1 ratio with 2× Laemmli buffer (#1610737, Bio-Rad, Calif., USA) followed by 15 mins of boiling. Samples were run in NuPAGETM 10% Bis-Tris Gels (Invitrogen, Calif., USA) using MOPS-SDS buffer [50 mM MOPS, 50 mM Tris, 1 mM EDTA, 0.1% (w/v) SDS] at 250 V for 30 mins. Gels were stained with Coomasie brilliant blue followed by overnight washing with a destaining solution (50% water, 40% methanol, 10% glacial acetic acid).

2.6. Immunoblot Analysis

For western blot, proteins were electroblotted onto a nitrocellulose membrane at 100 V for 1 hr. For dot blot, proteins were blotted on nitrocellulose membrane and were incubated for 30 mins at room temperature. Membranes were washed in deionized sterile water for 1 min and were directly blocked with 2% (w/v) BSA at 37° C. for 1 hr. Washing was performed thrice using PBS-T (PBS with 0.01% Tween-20). All detection followed the indirect format. Antibodies were added in 1:1000 dilution of PBS-B (PBS with 0.1% BSA) and incubated for 1 hr at room temperature. After washing, HRP-conjugated anti-murine IgGk antibody or avidin-conjugated HRP was added in 1:10,000 dilution of PBS-B and incubated for 1 hr at room temperature with constant shaking. Following washing, 1 mL of DAB substrate (D22185, Invitrogen, USA) was poured on the membrane. The reaction was stopped by adding excess PBS.

2.7. Capture ELISA

Ninety-six well ELISA plate was coated with 100 μL of either PD1 or TGFBR1 (1 μg/mL) for 16 hrs at 4° C. Coated wells were washed with PBS-T and blocked with 2% (w/v) BSA for 1 hr at 37° C. Fusion protein (1 μg/mL and 2 μg/mL) were diluted in PBS and 100 μl of these solutions were transferred into designated wells followed by incubation at room temperature for 1 hr. For detection of binding between TGF-B1 and TGFBR1, anti-PD-L1 was used as the primary antibody; while in the detection of PD-L1 binding with PD1, an anti-TGF-B1 antibody was used. Primary antibodies were added in 1:1000 dilution in PBS-B and incubated for 1 hr at room temperature. Following washing with PBS-T, HRP-conjugated anti-murine IgGk antibody was added in 1:10,000 dilution of PBS-B and incubated for 1 hr at room temperature. After washing, TMB peroxidase substrate (#555214, BD Biosciences, Calif., USA) and stop solution were added sequentially. Optical density (OD) reading was recorded at 450 nm. Normalization control used was the lack of receptor coating, a negative control was without the addition of the fusion protein, and antibody specificity controls included isotype anti-CD25 antibody without primary antibody.

2.8. Immunofluorescence Staining

CD25 expression in Jurkat cells was visualized using FITC-conjugated anti-CD25. Expression of PD1 and TGFBR1 in AMLK and HEK-Blue TLR2 cells were visualized using FITC-conjugated anti-PD1 and pre-mixed (1:1 ratio for 1 hr at room temperature) anti-TGFBR1 antibody with FITC-conjugated anti-mouse IgG antibody. Approximately $1 \times 10^6$ cells were collected by centrifugation followed by resuspension in 100 μL of PBS containing 1:100 dilution of antibody and incubated at 4° C. for 30 mins. Washing with PBS-T was performed twice by centrifugation at 500×g for 3 mins. Cells were incubated in 25 μL of PBS with or without 0.5 μg/mL Hoechst 33342 (H3570, Thermo Scientific, MA, USA) for 5 mins at room temperature. Cells were washed once with PBS and allowed to attach on poly-L-lysine coated slides before visualization under a fluorescence microscope.

2.9. Lipofection and Stable Transfection

TLR2-expressing HEK Blue cells ($1 \times 10^6$) were seeded in 6-well plates and cultured for 24 hrs. Lipofection with pCMV3-PD1 construct proceeded using Lipofectamine® 2000 (Invitrogen, Calif., USA) following the manufacturer's protocol using a 5 μg vector DNA to 10 μL Lipofectamine ratio. After 72 hrs of culture, transfected cells were selectively grown in the presence of 500 μg/ml of G418 (Invivogen, Calif., USA) for 1 week. Cells were then serially diluted into single cells in a 96-well plate to isolate stably transfected single-cell clones that homogenously express PD1 protein. Successful transfection and expression were assayed using immunofluorescence staining.

2.10. NF-κB-Induced—Secreted Embryonic Alkaline Phosphatase (SEAP) Assay

The absence of endotoxin was first examined in the isolated fusion protein using LAL assay (L00350, Genscript, USA). Lipofected HEK-Blue TLR2 cells were seeded in 96-well plates with $1 \times 10^5$ cell density per well. After 24 hrs, the medium was replaced with HEK Blue Detection Medium (PlasmoTestTM, Invivogen, Calif., USA) and the cells were challenged with an increasing dilution of mycobacteria-containing FCA (Freund's Complete Adjuvant) (#77140, Thermo Scientific, MA, USA) in 1:100, 1:1000, 1:10000, 1:50000 and 1:100000 dilutions. Cells were either directly treated with 50 ng/mL fusion protein or pre-incubated first with either 1 μg/mL of anti-PD1 or anti-TGFBR1 antibodies. Cells without FCA challenge served as the normalization control. After 24 hrs of incubation, NF-κB-induced secreted embryonic alkaline phosphatase (SEAP) activity was assessed by measuring optical density (OD) absorbance at 655 nm. Percent inhibition was derived using the formula: [(OD(−)TP− ODexperimental)/OD(−)TP*100].

2.11. Growth Suppression Assay

The growth suppression activity of fusion protein in PHA/IFN-γ-activated Jurkat cells was performed by incubating 100 ng/mL of fusion protein within a week. Growth suppression was compared to PD1-blocked (pre-incubated with 1 μg/mL anti-PD-1 antibody) and TGFBR1-blocked cells (pre-incubated with 1 μg/mL anti-TGFBR1 antibody) with untreated activated and non-activated cells as controls. Cell viability and cell count were assayed using trypan blue staining assisted by automated cell counter CountessTM (Invitrogen, Calif., USA) after 3, 5, and 7 days. Cells were fed every 3 days. Percent growth suppression was derived using the formula: [(untreated count—fusion protein-treated count)/untreated Jurkat cells)]*100.

2.12. Gene Expression Analysis

AMLK cells ($1.0 \times 10^7$) were cultured in 6-well plates and treated with 50 ng/mL of either fusion protein or commercially available TGF-B1 or PD-L1 for 32 hrs. Receptor-reconstituted HEK-Blue TRL2-expressing cells ($1.0 \times 10^6$) were cultured in 12-well plates and treated directly with 50 ng/mL fusion protein or following pre-incubation of receptor-specific antibodies. Jurkat cells (activated and non-activated, $1.0 \times 10^6$ each) were cultured in 6-well plates with supplementation of 50 ng/mL of fusion protein for 24 and 72 hrs. Set-ups without fusion protein served as control. RNA extraction proceeded with RNeasy® Mini Kit (Qiagen, Germany). For all samples, 1 μg of RNA was converted to cDNA using either M-MuLV Reverse Transcription kit (NewEngland Biolabs) or iScriptTM cDNA synthesis kit (Bio-Rad, Calif., USA) following the manufacturer's protocol. Gene expression analysis was carried out using either M-MuLV Reverse Transcription kit (NewEngland Biolabs) or iScript™ cDNA synthesis kit (Bio-Rad, Calif., USA) following the manufacturer's protocol. Gene expression analysis was carried out using SsoFast™ EvaGreen® Supermix (Bio-Rad, Calif., USA) with CFX96™ Real-Time PCR Detection System using primer pairs shown in Table 1. Amplification parameters include an initial denaturation at 96° C. for 30 sec followed by 40 cycles of denaturation at 96° C. for 5 sec, annealing and extension at 60° C. for 60 sec. Expression levels were presented as fold change values.

TABLE 1

Primer pairs used in gene expression analysis.

| Gene | Forward primer (5' to 3') | | Reverse primer (5' to 3') | |
|---|---|---|---|---|
| c-myc | CGTCCTCGGATTCTCTGCTC | (SEQ ID NO: 28) | GCTGGTGCATTTTCGGTTGT | (SEQ ID NO: 29) |
| bcl2 | TCCGCATCAGGAAGGCTAGA | (SEQ ID NO: 30) | AGGACCAGGCCTCCAAGCT | (SEQ ID NO: 31) |
| ifn-y | ACTGACTTGAATGTCCAACGCA | (SEQ ID NO: 32) | ATCTGACTCCTTTTTCGCTTCC | (SEQ ID NO: 33) |
| tgfb1 | GCGTGCTAATGGTGGAAAC | (SEQ ID NO: 34) | CGGTGACATCAAAAGATAACCAC | (SEQ ID NO: 35) |
| twist1 | TGCATGCATTCTCAAGAGGT | (SEQ ID NO: 36) | CTATGGTTTTGCAGGCCAGT | (SEQ ID NO: 37) |
| pik3ca | CCTGATCTTCCTCGTGCTGCTC | (SEQ ID NO: 38) | ATGCCAATGGACAGTGTTCCTCTT | (SEQ ID NO: 39) |
| akt1 | GCAGCACGTGTACGAGAAGA | (SEQ ID NO: 40) | GGTGTCAGTCTCCGACGTG | (SEQ ID NO: 41) |
| smad4 | GCTGCTGGAATTGGTGTTGATG | (SEQ ID NO: 42) | AGGTGTTTCTTTGATGCTCTGTCT | (SEQ ID NO: 43) |
| nfkb1 | GCAGCACTACTTCTTGACCACC | (SEQ ID NO: 44) | TCTGCTCCTGAGCATTGACGTC | (SEQ ID NO: 45) |
| foxp3 | GCTTCATCTGTGGCATCATC | (SEQ ID NO: 46) | TGGAGGAACTCTGGGAATGT | (SEQ ID NO: 47) |
| b-actin | TCACCCACACTGTGCCCATCTACGA | (SEQ ID NO: 48) | CAGCGGAACCGCTCATTGCCAATGG | (SEQ ID NO: 49) |

2.13. Cellular Retention Assay

TGFBR1+PD1+HEK293 cells ($5 \times 10^5$) were seeded into 96-well plates coated with 50 µg/mL poly-L-lysine (Scien-Cell, Calif., USA) and incubated for 10 mins on ice. Unwanted binding sites were blocked with 20% (v/v) FBS for 5 mins. Fusion protein (2 µg/mL) was added next and incubated for 10 mins followed by the addition of $5 \times 10^5$ TGFBR1+PD1− HEK293 cells and incubated further for 20 mins. The wells were gently washed once with 200 µL PBS to remove non-binding cells. Cellular retention was recorded as a measure of the total number of counted cells using trypan blue staining. Reverse retention assay was performed by first coating the substrate with the TGFBR1+PD1− cells followed by the addition of the TGFBR1+PD1+ cells. Without fusion protein, PD1-blocked and TGFBR1-blocked setups served as controls. Retention count was normalized using the count of HEK only (no binding partner) set-up.

2.14. Cellular Size-Exclusion Assay

TGFBR1+PD1+HEK293 cells ($5 \times 10^5$) were mixed with the same cell density of TGFBR1+PD1-cells in 0.5 mL of PBS with or without receptor blocking antibodies (anti-PD1 and anti-TGFBR1) and incubated for 10 mins on ice. Approximately, 0.5 mL of 2 µg fusion protein was added and incubated for 20 more mins. The solution was transferred into a new conical tube through a 20 µm cell strainer mesh. Cell count was determined using trypan blue staining. Set-up without fusion protein served as a negative control.

2.15. Fluorescence-Assisted Cell Counting

Initially, $1 \times 10^4$ of each activated and non-activated Jurkat T cells were separately stained with 0.5 µg/mL Rhodamine B (#83689, Sigma-Aldrich, MO, USA) and 0.5 µg/mL Hoechst 33342, respectively for 10 mins. Cells were washed with PBS and collected by centrifugation. Cells were mixed (1:1 ratio) in 100 µL PBS with 200 ng of fusion protein for 15 mins. The solution was transferred into poly-L-lysine-coated 96-well plates and cells were allowed to settle for 10 mins before paired-cell counting.

2.16. Co-Culture Assay

A 1:1 ratio ($1 \times 10^6$ each) of non-activated and PHA/IFN-γ activated Jurkat T cells were co-cultured in 24-well plates with 1 µg/ml of the fusion protein in the presence or absence of receptor blocking antibodies (anti-PD1 and anti-TGFBR1) for 24 hrs. Foxp3 expression was assayed by immunoblot and qRT-PCR. IL2Ra (CD25) was assayed quantitatively using Qubit 2.0 using excitation 430-495 nm/emission 510-580 nm filters.

2.17. Data Analysis

Statistical analyses were performed using Data Analysis Software (Microsoft, WA, USA) and Prism 5 software (GraphPad Software, Calif., USA). P-values less than 0.05 were considered significant. All analyses and p-values are described in figure legends.

3. Detailed Description of the Invention.

3.0 Summary—Fusion Gene and Protein Design, Construction, and Experimental Results:

The fusion TGF-B/checkpoint gene and protein constructs were based upon the DNA (SEQ ID NO: 2) and amino acid (SEQ ID NO: 14) sequences of the TGF-B1 ligand the PD-L1 immune checkpoint domain (SEQ ID NO: 6), and selected flexible peptide linker (GGGGS)3 linker (SEQ ID NO: 20) and a rigid peptide linker A(EAAAK)2A (SEQ ID NO: 27). The details of the ligand/receptor binding domain sequences are presented in the Sequence Listing:

The Nucleotide and Amino Acid Sequence Listings—the PatentIn Software was used to input nucleotide and amino acid sequences listings, and presented in ASCII text file, hereby directing its entry into the application and disclosing the Sequence Listing as follows:

i) Name of ASCII text file: SEQ-ID-App-17-248288-TGFB1-PDL1_ST25 ii) Date of Creation: Apr. 2, 2023 iii) Size of ASCII text file: 38,000 bytes

In an embodiment of the fusion protein, a TGF-B1/PD-L1 fusion protein (SEQ ID NO: 13) was molecularly designed and constructed with the fusion gene of TGF-B1 (SEQ ID NO: 2) (NM_000660.6) and PD-L1 (SEQ ID NO: 6) (NM_014143.3) using an overlap extension PCR strategy. A dimeric TGF-B1 (SEQ ID NO: 21) was successfully developed by incorporating a flexible (GGGGS)3 linker (SEQ ID NO: 20) between two monomeric units of PD-L1 (SEQ ID NO: 6) (GenBank accession: MN688294) and linked with a rigid linker A(EAAAK)2A (SEQ ID NO: 27) upstream of the PD-L1 domain (SEQ ID NO: 6) (GenBank accession: MN688295) as graphically represented in FIG. 1A.

The fusion gene (SEQ ID NO: 1) was cloned into a pCDNA3.1+ mammalian expression vector (pCDNA3.1+/TP) and the fusion gene with vector construct was transfected into HEK293 (Human Embryonic Kidney) cells by lipofection. After 48 hrs, cell lysates of transfected cells were analyzed. The presence of a thicker 70 kDa protein band (FIG. 1B) in pCDNA3.1+/TP compared to the control suggested the successful expression of the fusion protein and confirmed by antibody and ligand binding experiments.

The fusion protein (SEQ ID NO: 13) was immunoprecipitated from the lysate using magnetic beads with covalently coupled antibodies against PD-L1 and TGF-B1, and we verified that this 70 kDa protein was the desired fusion product. SDS-PAGE analysis (FIG. 1C) was consistent with the fusion of the TGF-B1 and PD-L1 domains in this protein. Molecular size comparisons of the fusion protein with a mammalian-derived full-length PD-L1 (FIG. 1D) revealed that our fusion protein has the molecular weight expected of the fusion of PD-L1 extracellular domain (SEQ ID NO: 6) with TGF-B1 dimer (SEQ ID NO: 21). These data support the successful development of a novel TGF-B/Immune checkpoint fusion protein (SEQ ID NO: 13) (FIG. 1E).

3.1. Development of TGF-B/Checkpoint Fusion Proteins—Based Upon Ligand/Receptor Binding Domains.

1) SEQ ID NO:1 in the Sequence Listing shows that the DNA sequence of the TGF-B1/PD-L1 fusion gene comprising of two TGF-B1 monomers (SEQ ID NO: 2) linked together with the flexible linker (SEQ ID NO: 20) to form a TGF-B1 dimer (SEQ ID NO: 21) and linked with a rigid spacer (SEQ ID NO: 27) to a PD-L1 domain. The amino acid sequence for this construct is shown in SEQ ID NO: 13 in the Sequence Listing. This construct is also shown schematically in FIG. 12a in the Drawings.

Selected Domains for construction of the fusion protein. The Sequence Listing indicates the DNA and Amino Acid domains selected from the gene and protein structures of:

2) TGF-B1 (SEQ ID NO: 2) (NM_000660.6)— the DNA coding sequence of TGF-B1 is 1173 nucleotides in length with a protein sequence of 391 amino acids. For our unique construct, we selected a particular domain with a nucleotide sequence (SEQ ID NO: 2—TGF-B1 monomer) with an amino acid sequence—(SEQ ID NO: 14).

In some embodiments, the DNA and amino acid sequences of the TGF-B1 domain, partly or wholly overlap with the enumerated DNA (SEQ ID NO: 2) and amino acid (SEQ ID NO: 14) sequences or represent variants of the DNA (SEQ ID NO: 2) and amino acid (SEQ ID NO: 14) sequences capable of binding to its receptor.

3) The DNA coding sequence of the flexible peptide linker SEQ ID NO: 5 consisted of a (GGGGS)3 linker, with amino acid sequence SEQ ID NO: 20 which we selected based on maintaining the flexibility of the two TGF-B domains that it links, wherein the conformation of the TGF-B ligand allows binding to TGF-B receptors.

In some embodiments, the flexible peptide linker SEQ ID NO: 20 is a variant of the enumerated DNA (SEQ ID NO: 5) and amino acid (SEQ ID NO: 20) sequences or composed of linkers with different amino acid lengths and sequences, while retaining flexible characteristics, wherein the conformation of the TGF-B ligand allows binding to TGF-B receptors.

4) PD-L1 (SEQ ID NO: 6) (NM_014143.3)— the DNA coding sequence of PD-L1 is 822 nucleotides in length with a protein sequence of 273 amino acids. For our unique construct, we selected a particular domain with nucleotide sequence (SEQ ID NO: 6 –PD-L1) with an amino acid sequence (SEQ ID NO: 17).

In some embodiments, the DNA and amino acid sequences of the PD-L1 domain, partly or wholly overlap with the enumerated DNA (SEQ ID NO: 6) and amino acid (SEQ ID NO: 17) sequences or represent variants of the DNA (SEQ ID NO: 6) and amino acid (SEQ ID NO: 17) sequences capable of binding to its receptor.

5) The amino acid sequence of the flexible peptide linker (SEQ ID NO: 20) consisted of a (GGGGS)3 linker which had been used in other constructs to create functional scFvs and which we selected based on maintaining the flexibility of the two TGF-B domains that it links, wherein the conformation of the TGF-B ligand allows binding to TGF-B receptors.

In some embodiments, the flexible peptide linker is a variant of SEQ ID NO: 20 or composed of linkers with different amino acid lengths and sequences, while retaining flexible characteristics, wherein the conformation of the TGF-B ligand allows binding to TGF-B receptors.

6) The amino acid sequence of the rigid peptide linker SEQ ID NO: 27 was derived from the sequence A(EAAAK)2A upstream of the PD-L1 domain (SEQ ID NO: 6) (GenBank accession: MN688295) and was selected based on preventing allosteric interference between the TGF-B ligand and the immune checkpoint domain that it links, wherein the conformation of the fusion protein allows binding to TGF-B and immune checkpoint receptors, respectively.

In some embodiments, the rigid peptide linker is a variant of SEQ ID NO: 27 or composed of linkers with different amino acid lengths and sequences, while preventing allosteric interference between the linked TGF-B ligand and the immune checkpoint domain, wherein the conformation of the fusion protein allows binding to TGF-B and immune checkpoint receptors, respectively. 3.2. The dimeric TGF-B1 domain (SEQ ID NO: 21) of the fusion protein binds to TGF-B1 receptors only in the presence of co-receptors as shown by co-immunoprecipitation (co-IP) and immunoblot with TGFBR1 from leukemic cells.

Dimerization of endogenous TGF-B1 is needed to assume its active form, which may consist of homodimers but mature TGF-B dimers may also form heterodimers of TGF-B1 with other TGF-B monomers including TGF-B2 and TGF-B3 [38-39]. We recreated the dimer (SEQ ID NO: 21) by linking two monomers with (GGGGS)3 linker (SEQ ID NO: 20) which is used to link functional scFvs. Comparison of the predicted structure of fused TGF-B1 with an NMR-derived structure (PDB ID:1KLD) using Phyre2 revealed a more concave configuration in the former (FIG. 2A) probably due to the flexibility of the linker (SEQ ID NO: 20). However, this structure is also observed in bone morphogenic proteins (BMPs), a class of cytokines that also belong to the TGF-B superfamily [38-39].

"Fingertip" structures responsible for receptor binding are shown (FIG. 2B). We have not found prior accounts of engineering a dimeric TGF-B1 (SEQ ID NO: 21) which may explain the lack of clear structure predictions. To test the usefulness of constructing the dimeric TGF-B ligand (SEQ ID NO: 21), its binding to TGF-B receptors and co-receptors was examined to confirm that the constructed dimeric TGF-B ligand in the fusion protein exerted biochemical and biological activity.

TGF-B1 signals through oligomerization with type I and type II receptors [38-39]. Binding studies suggested the chronologic interaction first of a type II receptor such as TGFBR2 followed by association of type I receptors such as TGFBR1. These co-receptor binding experiments were important to confirm the proper conformation of dimeric TGF-B ligand fused to an immune checkpoint domain. First, it was established that the fusion protein was unable to bind TGFBR1, by itself, in the absence of co-receptors. This lack of direct interaction of between the fusion protein (SEQ ID NO: 13) and TGFBR1 was tested (FIG. 3A) using co-immunoprecipitation (co-IP) and reverse co-IP experiments followed by immunoblot analysis. Results of dot blot analysis (FIG. 4A) showed that when anti-TGFBR1 antibody was used to co-precipitate the two proteins, TGFBR1 but not TGF-B1 was detected. Also, when anti-TGF-B1 antibody is used, TGF-B1 but not TGFBR1 was detected. These results were consistent with the results of reverse co-IP. To eliminate false positives, we first noted the absence of endogenous TGF-B1 (molecular weight is 25 kDa) in our expression system through Western blot (FIG. 3B) and TGF-B1 but not TGFBR1 was detected in pCDNA3.1+/TP-transfected (TR) cells (FIG. 4A) indicating the absence of contamination. These results indicate that the fusion protein (SEQ ID NO: 13) does not bind TGFBR1 directly but only binds TGFBR1 in the presence of other co-receptors. These results are consistent with the involvement of co-receptors including type II receptors, in addition to type I receptors in the binding of TGF-B1, further supported by immunoprecipitation, immunoblot, and cellular binding data (FIG. 3, FIGS. 4*a-e* and FIG. 5).

The result of capture ELISA experiments revealed no significant difference in the binding readout of set-ups with the fusion protein (+TP) and the controls (FIG. 4B) which is consistent with previous experiments using SPR (surface plasmon resonance) that yielded undetectable binding using TGFBR1 alone. To reason out the absence of binding was due to the requirement for co-receptors and not because of structural defects, we performed co-IP in the presence of other co-receptors. Due to the unavailability of type II-specific antibodies, we used the lysate of leukemic cells which express both TGFBR2, TGFBR1, and other co-receptors. Co-IP results as shown by denaturing gel in FIG. 4C show the presence of three co-receptor binding partners. Dot blot analyses in FIG. 4D and Western blot analysis in FIG. 3B show the successful interaction of the fusion protein with co-receptors. Thus, the fusion protein binds TGFBR1 only in the presence of other co-receptors. These results show the ability of dimeric TGF-B1/PD-L1 fusion protein (SEQ ID NO: 13) to bind TGF-B co-receptors comparable to the binding reactions of endogenous TGF-B1 protein (FIG. 4E).

3.3. PD-L1 Domain (SEQ ID NO: 6) of the TGF-B1/PD-L1 Fusion Protein (SEQ ID NO: 13) Binds PD1 Receptor.

Next, PD-1 binding by the fusion protein was examined using the same co-precipitation experiments; for this experiment, a commercially available active PD-1 protein was used. As control, the absence of endogenous PD-L1 expression (molecular weight is within 45-70 kDa depending on glycosylation state) in transfected (TR) cells (FIG. 2C) was demonstrated, indicating the absence of contaminating signals. The binding interaction between the fusion protein and PD1 was indicated by the presence of band sizes corresponding to both proteins in denaturing gels (FIG. 3C) which corroborate the presence of signal from these two proteins in dot blot (FIG. 5A) and western blot (FIG. 3B) analyses. This finding is consistent with results obtained in capture ELISA assays (FIG. 5B) where a higher TGF-B1 (fused) signal was observed in fusion protein-treated set-up in a concentration-dependent manner. These data suggest the ability of the PD-L1 domain (SEQ ID NO: 6) of the fusion protein (SEQ ID NO: 13) to bind PD1.

3.4. Expression of Immune-Related Genes was Coordinated Through Actions of the TGF-B1/PD-L1 Fusion Protein (SEQ ID NO: 13).

To support findings of these protein-protein interaction, experiments we done separately treating TGFBR1+PD-1+ leukemic (AMLK) cells (FIG. 6A) with the fusion protein, TGF-B1 and PD-L1 followed by gene expression analysis of immune-related genes (c-myc, bcl2, foxp3, tgfb1, ifn-γ, twist1, pik3ca, akt1,5smad4). Set-up without treatment with the fusion protein served as a normalization control. We found that Cq values of B-actin in all set-ups were comparable (FIG. 6B) indicating similarity in template concentration. Relative fold change expression (Table 2) showed that treatment of fusion protein and TGF-B1 upregulated all these genes. PD-L1 treatment upregulated c-myc, ifn-γ, akt1, and smad4 only while the rest are downregulated. A comparison of relative gene expression levels in the three experimental set-ups suggest the balancing of fold change value in the fusion protein-treated set-ups against treatments with unfused TGF-B1 and PD-L1. Higher fold change values were observed in the TGF-B1-treated set-up compared to PD-L1-treated. However, treatment with fusion protein balanced out this difference (FIG. 5C), and the expression profile was found to be sandwiched between the two (FIG. 5D). The normalization of readout found in fusion protein-treated cells captured the combined expression signature in TGF-B1 and PD-L1-treated set-ups, suggesting the functional binding of the two domains of the fusion protein that are potentially similar to the endogenous forms.

TABLE 2

Fold change expression of immune-related genes in AMLK cells treated with the fusion protein, TGF-B1/PD-L1.

| Gene Targets | Fusion protein | TGF-B1 | PD-L1 |
|---|---|---|---|
| c-myc | 13.97717 | 26.35491 | 1.239708 |
| bcl2 | 6.364292 | 12.21007 | 0.622006 |
| foxp3 | 3.226567 | 5.755734 | 0.590496 |
| tgfb1 | 2.181015 | 4.658934 | 0.444421 |
| ifn-y | 6.868523 | 10.19649 | 1.283426 |
| twist1 | 3.446185 | 6.868523 | 0.202361 |
| pik3ca | 7.490178 | 9.285631 | 0.792784 |
| akt1 | 6.233317 | 30.59025 | 3.494292 |
| smad4 | 10.51954 | 26.72281 | 1.536875 |

3.5. TGF-B1/PD-L1 Fusion Protein (SEQ ID NO: 13) Inhibits Inflammatory Gene NF-κB Activation and Signaling.

As a potent activator of inflammatory genes, NF-κB signaling plays a critical role in inflammation and is believed to contribute strongly in the pathology of immune dysregulation and autoimmune diseases [33-34]. As an initial assay to evaluate the potential use of our fusion protein as anti-inflammatory therapy, the fusion protein's ability to suppress NF-κB activation was tested by challenging commercially available human TLR2-expressing HEK-Blue cells with Freund's Complete Adjuvant (FCA). In this system, the Secreted Embryonic Alkaline Phosphatase (SEAP) gene is expressed under the control of NF-κB-responsive promoter and the activation of TLR2 signaling by FCA induced SEAP secretion in the culture. TLR-2 is sensitive to bacteria-derived molecules, although mammalian cells were used, it was confirmed in these experiments that endotoxins were absent in the fusion protein preparations used in all in-vitro assays.

As expected, TGFBR1 but not PD-1 was expressed by these cells due to the cell type-specific expression of the latter, revealed by immunofluorescence staining (FIG. 7A). Lipofection of these cells with a full-length PD-1 cDNA cloned in pCMV3 yielded stable expression (FIG. 7A). SHP1/2-mediated PD1 signaling has been found to induce many of its intracellular signaling events and such protein was found to be expressed and functional in HEK-293 cells. SHP1/2 signaling was also found to be activated by the TLR2 pathway making the SEAP assay a conducive reporter strategy to study NF-κB activation by these two proteins.

After reconstituting the receptors of TGF-B1 and PD-L1, the cells were treated with 1:100 dilution of FCA in the presence of commercially available anti-*mycoplasma* agent, Normocin to prevent false-positive reading. The optical density (OD) at 655 nm was measured after 24 hrs to measure SEAP secretion in the culture supernatants. Cells treated with fusion protein showed 73.66% inhibition of SEAP secretion relative to the untreated set-up (FIG. 7B and FIG. 8A). Incubation of the cells with anti-TGFBR1 or anti-PD-1 antibodies before fusion protein treatment resulted in more permissive NF-KB activation correlating to lower SEAP inhibition (PD1 Ab=35.91%, TGFBR1 Ab=28.51%) (FIG. 7B and FIG. 8A), suggesting the downregulation of NF-κB activation by the fusion protein and demonstrate an additional proof that the PD1 receptor can be studied functionally in this model.

To correlate the functionality of this NF-κB signaling inhibition, the expression of NF-κB target genes, c-Myc, and Bcl2 was evaluated. Consistent with NF-kB downregulation, these genes were found to be downregulated in fusion protein-treated (+TP) set-up relative to untreated (broken line), suggesting the downregulation of NF-κB signaling by the fusion protein. Treatment with receptor-specific antibodies nearly restored the expression profile similar to the untreated (FIG. 7C). These findings confirmed that the TGF-B1/PD-L1 fusion protein inhibited NF-κB signaling.

3.6. The TGF-B1/PD-L1 Fusion Protein (SEQ ID NO: 13) does not Abrogate NF-κB Signaling in the Presence of a Low Concentration of Inflammatory Signals The concentration-dependence of NF-κB signaling inhibition of fusion protein was tested by increasing FCA dilution to 1:1,000, 1:10,000, 1:50,000 and 1:100,000. After 24 hrs, we found significant reduction in SEAP secretion of cells treated with fusion protein (+TP=0.3473) compared to the control (−TP=0.6773) in 1:1,000 dilution. This significant reduction was constantly observed in the rest of other dilutions, demonstrating additional evidence of the potential anti-inflammatory activity of our fusion protein (FIG. 7D).

Decreasing the inflammatory trigger did not abrogate SEAP secretion even at 100,000-fold dilution of FCA. Treatment with receptor-specific antibodies resulted in SEAP secretion that was higher in those set-ups compared to +TP alone, suggesting receptor-specific activities. Significant inhibition was only observed in 1:1,000 FCA dilution (IB PD1/+TP=26.34%, IB TR/+TP=25.53% and +TP=47.83%) (FIG. 8B) and no difference was observed in higher dilutions. Interestingly, we found a 60-70% inhibition of SEAP secretion in all dilutions treated with the fusion protein (FIG. 7E), suggesting a basal of 30-40% inflammatory permissive response by the fusion protein. This data suggests that while inflammation is reduced, NF-κB signaling is not completely abolished. This is an attractive strategy for immune regulation that avoids toxicity from excessive immune suppression while on therapy using the TGF-B1/PD-L1 fusion protein (SEQ ID NO: 13).

3.7. TGF-B1/PD-L1 Fusion Protein (SEQ ID NO: 13) Selectively Suppressed Growth of Activated Jurkat T Cells by.

The functional consequences of receptor binding by fusion protein were evaluated in response to the growth of activated effector-like Jurkat T cells which have an endogenous expression of TGF-B receptors. The induction of PD-1 expression in Jurkat cells was accomplished with PHA and IFN-γ. Although PHA alone was found to induce mitogenic effects on lymphocytes, its proliferative effects on Jurkat cells were negligible. Co-activation of effector phenotype was done with a pro-inflammatory stimulant such IFN-γ in nanogram concentration. This activation was used to assess the immune downregulation activity of fusion protein against activated effector T cells. Viable cell count was assayed using trypan blue staining assisted with an automated cell counter. After 3 days of culture, a significant reduction of viable cell count of activated (PHA/IFN-γ-treated) Jurkat cells was observed compared to non-activated cells (804,000 vs. 1,126,000) in the presence of fusion protein (FIG. 9A). However, comparable viability was observed in the presence of anti-PD1 or anti-TGFBR1 antibodies. These data suggest the selective cellular growth inhibition of activated effector-like Jurkat cells by the fusion protein.

3.8. The Constructed Fusion Protein (SEQ ID NO: 13) Counteracts Effector Activation and Sustains Cell Growth Suppression in Activated Jurkat T Cells To determine whether the suppression in cell growth is temporary or constant, activated Jurkat cells were cultured with the fusion protein (+TP) for 1 week and the growth response was compared to cultures in the absence of fusion protein (−TP) after 3, 5, and 7 days. FIG. 9B shows that there was a significant growth suppression in +TP compared to those in −TP (804,000 vs. 1,453,000, respectively). This significant reduction in viable cell count was also observed after 5 (694,000 vs. 1,526,000) and 7 days (650,000 vs. 1,480,000) of culture. Immuno-blocked set-ups (IB TR/+TP and IB PD1/+TP) revealed that this reduction in the viable cell count was due to the binding of fusion protein domains with their cognate receptors. Phytohemagglutinin (PHA) is a mitogenic agent that binds CD3, however, it is interesting to assess if the suppression is co-receptor-dependent, since T cell activation requires a signal from co-receptors such as CD28. However, this result suggests the ability of fusion protein to counteract PHA/IFN-γ-induced activation and sustain growth suppression in activated effector immune cells.

3.9. TGF-B1/PD-L1 Protein (SEQ ID NO: 13) Induces Reversal of PHA/IFN-γ Activation and Induction of Regulatory T Cell Differentiation.

Further experiments indicated that the reduction in cell viability was a result of the induction of T cell anergy as a consequence of PD-1/PD-L1 pathway activation or metabolic termination for induced Treg (iTreg) differentiation elicited by TGF-B1 signaling. First, we correlated the cell count data from the seven days culture experiment above. A significant increase in cell count was observed in −TP, IB TR/+TP, and IB PD1/+TP. Comparable cell count was observed in +TP (FIG. 8C) which coincides with sustained growth suppression of cells after 7 days of culture (FIG. 8D). This suggests the induction of cell cycle arrest by the fusion protein, which may suggest the anergy or reversal of mitogenic activities by PHA.

Next, the expression levels of nfkb1 and foxp3 were measured to assess iTreg induction. After 24 hrs of culture, in +TP and −TP, the upregulation of nkfb1 was observed which plays a vital role in both regulatory and effector functions of T cells. However, nfkb1 expression in +TP set-up (6.521-fold expression) was lower compared to −TP (15.846-fold expression) (FIG. 9C) which may indicate induction of cell fate with lower inflammatory potential by the fusion protein. This data is consistent with observations of higher foxp3 expression in +TP (2.362-fold increase) compared to −TP set-up (with reduced expression in a factor of 0.518 or nearly 2-fold decrease), suggesting the ability of fusion protein to counteract the activation of effector cell and induce differentiation of cells with much higher anti-inflammatory activities. This expression signature was similar after 72 hrs of culture where +TP had a 4.028-fold expression of nfkb1 which is lower than the 16.669-fold expression in −TP set-up. Foxp3 expression is higher in +TP cells with a 2.704-fold increase compared to −TP which reduced expression by a factor of 0.76. These relative mRNA expression values were similar at the protein level captured in a western blot analysis utilizing cell lysates after 72 hrs of culture. Consistent with the decrease in the inflammatory potential of cells treated with the fusion protein, intracellular IL-6 was found to be reduced compared to the controls (FIG. 9D). These findings suggest the anti-inflammatory activity of fusion protein by reversing T cell activation while favoring T regulatory cell differentiation.

3.10. Bi-Functional Bridging of the TGF-B1/PD-L1 Fusion Protein (SEQ ID NO: 13) Mediates Cell-to-Cell Interaction.

Bi-specific scFv or BiTE (bispecific T cell engager) technology facilitates the interaction of cytotoxic lymphocytes with cancer cells to induce tumor killing. TGF-B1 receptors are expressed on regulatory T cells while high PD1 expression was observed in activated effector cells systems. Meanwhile, activated regulatory T cells also express PD1; and TGF-B1 receptors were also found on effector cells. The molecular design of the fusion protein can act similarly as BiTE to potentially facilitate Treg-mediated contact-dependent immune regulation by cell-to-cell contact.

This bi-functional bridging activity was evaluated in a cellular retention assay by measuring the frequency of interaction between TGFBR1+PD1+ and TGFBR1+PD1− HEK293 cells (FIG. 10A). Normalized cellular retention of TGFBR1+PD1− cells with the substrate attached TGFBR1+ PD1+HEK-293 cells showed significantly higher cell count in +TP (256,333 retention count) compared to −TP (121,000 retention count) and receptor blocked set-ups (103,300 for IB PD1 and 93,667 for IB TR) as shown in FIG. 10B. This pattern was also observed in the reverse retention assay (268,667 retention in +TP; 128,000 in −TP, 152,667 in IB PD1/+TP and 138,333 in IB TR/+TP). We also found that treatment of these HEK-293 cells with fusion protein decreased the number of cells that passed through a 20 μm mesh strainer (FIG. 10C), as a result, +TP set-up has significantly lower count than the −TP set-up (FIG. 10D), suggesting the higher frequency of cell population trapped in the mesh due to cell-to-cell contact. These results suggest the ability of the TGF-B1/PD-L1 fusion protein to mediate cell-to-cell interaction.

While most BiTE platforms strategize on cell-to-cell contact to induce tumor killing by effector T cells, the design of the TGF-B1/PD-L1 fusion protein and the molecular expression of receptor targets could favor the recognition of effector T cells by the regulatory cells. To partially test this hypothesis, PHA/IFN-γ-activated and non-activated Jurkat T cells were separately labeled with Rhodamine B and Hoechst 33342, respectively before mixing in the presence or absence of our fusion protein. The results showed a higher pairing count (FIG. 10E) of Rhodamine B/Hoechst 33342-labeled cells in fusion protein-treated cell (+TP) versus the control (191 count vs 46, respectively) as shown in FIG. 10F. Co-culture set-up treated with fusion protein resulted in higher expression of foxp3 as analyzed by qRT-PCR and Western blot (FIG. 6G) and IL2Ra (CD25) measured fluorescently (FIG. 10H). These data suggest the ability of the TGF-B1/PD-L1 fusion protein (SEQ ID NO: 13) to potentially enhance Treg activities and induce a BiTE-like mechanism to facilitate Treg-mediated contact-dependent immune regulation which is a promising therapeutic strategy for autoimmune diseases.

4. Descriptions of the Subject Matter and Significance of this Invention:

Molecular crosstalk between effector immune cells and inhibitory cytokines or contact with regulatory cells are important mechanisms by which the immune response is regulated and controlled. These mechanisms are crucial in maintaining tolerance for self-antigens, preventing the onset of autoimmune disease (AID). TGF-B1 ligands can exert immunosuppressive properties by enhancing regulatory T cell activities whereas and PD-L1 can act by modulating the activation state of effector cells. TGF-B1 may be an important molecular target for autoimmune diseases such as inflammatory bowel diseases, type 1 diabetes, lupus, and other autoimmune diseases. Although the immunoregulatory activity of PD-L1 has been described a few decades ago, its application as a therapeutic target for AID is only in its early stages. Meanwhile, advancements in cancer immunotherapy have brought new classes of biologics that have shown encouraging clinical outcomes such as the BiTE or bispecific T cell engager. This strategy mediates the recognition of cancer by cytotoxic lymphocytes due to the dual specificity of the two scFvs against a cancer-associated antigen and a T cell surface marker. This cell-to-cell contact seems to capture Treg-mediated contact-dependent immune regulation that could be harnessed potentially as a strategy to downregulate autoreactive cells in AID. To validate these concepts, we a bifunctional TGF-B1/PD-L1 fusion protein was constructed. The description herein indicates the potential therapeutic applications of this fusion protein as an approach to treat immune dysregulation and autoimmune diseases (FIG. 11). A bifunctional TGF-B1/PD-L1 fusion protein was demonstrated to bind the target receptors, TGF-B receptors, and PD-1 and to work in concert to regulate immune effector cells.

Critical to the pathogenesis of immune dysregulation and autoimmune diseases, NF-kB is a transcription factor that is considered as a master regulator of immune response that targets many genes encoding pro-inflammatory proteins and that is known to be pathologically activated in many autoimmune conditions [3-5]. Many immunosuppressive drugs act on various stages of NF-kB signaling pathway and can be considered as an important biomarker to evaluate immunosuppressive properties of many biological therapies

[7-11]. The experimental results detailed herein indicate that activation of signaling pathways by these two ligands led to the downregulation of NF-kB signaling. Consistent with this, 73.66% relative inhibition of NF-kB activation was observed in SEAP reporter assays which collaborates to downregulate NF-kB-target genes, c-myc, and bcl2.

The activation of NF-kB is indispensable to the effector phenotype of T cells [10-11]. The biological activity of TGF-B1/PD-L1 fusion protein was tested to determine the correlation of NF-kB-dependent c-myc and bcl2 downregulation Jurkat T cells. The hypothesis being tested was whether the downregulation of these cell growth-promoting and anti-apoptotic proteins results in the suppression of cell growth and viability of stimulated effector cells. Several stimulatory molecules such as PMA, ionomycin, polyclonal CD3, and CD28 antibodies were used to induced T cell expansion, but PHA and IFN-γ were most consistent in inducing PD-1 expression in Jurkat T cells and were both found to activate NF-kB signaling. Consistent with the inhibition of NF-kB activation in reporter cells, only those stimulated with PHA and IFN-γ were found suppressed in terms of cell viability, and no significant increase in cell count was observed within 7 days of culture. Although the response in non-activated cells may be due to lack of PD-1 expression, receptor blocking using anti-TGFBRI or anti-PD-1 antibodies resulted in comparable cell viability and cell count, suggesting receptor-ligand-specific outcomes. This induction of reduced viability and unresponsiveness to stimuli may indicate passive regulation of immune response by TGF-B1 and PD-L1 signaling to control autoreactivity (FIG. 11A).

Regulatory T cells are considered indispensable to maintain immune tolerance (FIG. 7C). There is a growing interest in immunosuppressive or regulatory immune cell-based therapy for immune disorders. However, the success of regulatory T cell-based therapy remained disappointing as of today. Strategies to promote the expansion and enhancement of these suppressive functions by Treg is a promising approach. TGF-B1 has been shown to participate in the development of naturally occurring Tregs (nTregs) in the thymus and the differentiation of naïve CD4+ T cells to induce regulatory phenotypes in the periphery (iTregs) while PD-L1 is implicated in the latter development. Downregulation of NF-kB1 expression coincides with the reduced expression of intracellular IL-6 with subsequent increase expression of a Treg master regulator, Foxp3. Treg development involves stabilization of cytokine signals such as IL-2 and the requirement of Treg-specific CpG hypomethylation. The cellular interactions of TGF-B1/PD-L1 fusion protein on iTreg induction points to a potential role in immune regulation mediated by Treg cell. Different autoimmune types may involve different subtypes of T cells. In this regard, TGF-B1 has contrasting effects on immune cells and was found to promote Th17 and Th9 responses. As fusion partner, the PD-L1, has the capacity to downregulate these other T cell subsets.

There are more than 80 clinical subtypes of immune disorders and autoimmune diseases [1,10]. The majority of therapeutically approved biological drugs for autoimmune diseases address only a few of these types. Modes of action by these targeted-based therapies include depleting specific T and B cell subsets, neutralizing activities of inflammatory factors, or mediating receptor-ligand interactions. However, the long-term efficacy and sustained safety of these treatments are still in question. In addition to the deleterious side effects of small molecule drugs, efforts to create a more strategic therapy is valuable for immune disorders. In addition to its immune regulatory activity, the TGF-B1/PD-L1 fusion protein was tested in dose-dependent and time-dependent experiments to determine dose-controlled modulation of immune reactions that would be important in clinical safety. The TGF-B1/PD-L1 was shown to have NF-kB activation which has a permissive activity of around 30% regardless of the concentration of inflammatory triggers. This NF-kB-dependent c-myc and bcl2 downregulation increased over 7 days and approximately 50% of growth inhibition was observed with the fusion protein treatment. Although these data were derived in vitro, the use of an appropriate model and the execution of a comprehensive dosing experiment to assess avoidance of complete immunosuppression that would be important in adjustments of clinical dosing.

Aside from immune cells, other tissues of the body express TGF beta 1 receptors [12]. Being a pleiotropic cytokine, TGF beta 1 plays a role in the growth and differentiation of many cells of the body. In some tissues, TGF beta 1 promotes fibrosis and could potentially be involved in cancer progression. Many cancer treatment adjuvants include the sequestration or downregulation of TGF beta 1 activities. The biological half-life and potential tissue-distribution of the fusion protein are important factors to consider in therapeutic applications. Experiments on dosing are also a crucial part of physiological assessments of the toxicity of this recombinant protein. In the context of controlling tissue-specific autoreactivity, the distribution of the fusion protein may help in tissue recovery while allowing potential control of tissue/organ-reactive immune cells as cooperatively induced by the immunosuppressive activities of TGF beta 1 and PD-L1.

Recently, efforts by scientists to create and advance treatments for cancer have encouraged the spur of many immunotherapies that are now revolutionizing the way various cancers are treated. Chimeric antigen receptor T cell (CAR-T) therapy has been used to direct depletion of certain immune cells causing chronic inflammation which are now tested in clinical trials. Another platform, the BiTE (bispecific T cell engager) technology has been creating a milestone in cancer therapy.

Using a different approach, the current invention points to the potential application of fusion protein as BiTE technology for immune disorders and autoimmunity. The structural, receptor-binding ability and biological activity of TGF-B1/PD-L1 fusion protein described herein demonstrates its potential for immune regulation and control based upon several experimental observations. There was efficient binding to receptors expressed by both effector and regulatory cells. Further, the fusion of these two ligands enhanced Treg-mediated contact-dependent immune regulation through a BiTE-like mechanism (FIG. 11B). The TGF-B1/PD-L1 fusion protein (SEQ ID NO: 13) elicited a high frequency of cell-to-cell contact as determined in cellular retention, size exclusion, and co-culture assays. hese cell-to-cell contacts induced higher expression of Foxp3 and IL2Ra in vitro. It would be interesting to analyze the single-cell profile of marker expression in addition to population-wide quantification. Tregs represent a novel target in autoimmunity due to their dominant tolerance property. A small population of CD4+ and CD8+ T cells with autoreactivity to many antigens in the pancreas can reverse diabetes using only a few thousand Treg cells. The results of our co-culture assays demonstrate this dominant tolerance property where a mix of activated and non-activated Jurkat cells with fusion protein led to the upregulation of Treg-associated markers, IL2Ra, and Foxp3.

The molecular bioactivity of the fusion protein with the endogenous receptors are important for designs of potential therapeutic applications. The results of the biochemical and molecular assays herein demonstrate the similarity of our fusion protein with the endogenous unfused forms in terms of receptor binding, functional induction of gene signatures including cellular consequences of cell signaling activation. The experimental results using the fusion protein also point to the molecular signaling crosstalk between these proteins that are only beginning to be unraveled. Although Tregs represent a strategic target in AID, discouraging results have been produced in clinical settings so far. The fusion protein may represent a new class of therapy that could potentially help advance this regulatory cell-based targeted therapy in autoimmunity. The TGF-B and immune checkpoint domains of fusion protein work cooperatively to elicit both Treg-dependent and -independent mechanisms (FIG. 11) leading to downregulation of inflammatory responses. These findings may lead to promising approaches for the development of new therapies for autoimmune diseases.

There are several potential applications for the immune-regulatory activity of this novel TGF-B/Immune checkpoint fusion gene and protein, including treatment for:
1. patients with autoimmune diseases,
2. patients with immune dysregulation conditions,
3. patients who are unable to tolerate toxicities of existing immune therapies
4. patients who develop resistance to existing immune therapies
5. patients who develop toxicity from immune reactions as a result of immunotherapies with immune checkpoint inhibitors.
6. patients who develop toxicity from immune disorders, immune reactions, and immune dysregulation, inflammatory reactions, cytokine release syndromes, as a result of Chimeric Antigen Receptor T (CAR-T) cell treatments, other treatments with adoptive T Cells, Natural Killer (NK) Cells and Natural Killer T (NKT) Cells, Cytokine Induced Killer (CIK) Cells, Dendritic Cells, Tumor-Infiltrating Lymphocytes (TIL) and other immune-stimulating cellular treatments.
7. patients who develop immune disorders, immune reactions, immune dysregulation, inflammatory reactions, cytokine release syndromes from infectious illnesses such as COVID-19, other coronoviruses, influenza, other viral illnesses, bacterial, fungal and parasitic diseases, including syndromes associated with sepsis.

PATENT REFERENCE (Cited by Examiner)

[A] US 2013/0039911 A1 (Bedi et al., published 14 Feb. 2013).

Bedi at al., disclose a fusion protein with only one copy of TGF-B1 with the same sequence as instant SEQ ID NO: 14, a flexible linker with the same sequence a instant SEQ ID NO: 20, an immunoglobulin Fcv domain, and PD-L1 sequence the same as instant SEQ ID NO: 17. However, Bedi et al. do not disclose nor suggest a rigid peptide linker as indicated in the instant SEQ ID NO: 27, nor do they disclose or suggest a TGF-B1 homodimer linked by a flexible linker as indicated in the instant SEQ ID NO: 20. Thus, the instant application is free of prior art.

LITERATURE REFERENCES

[1] P. Li, Y. Zheng, X. Chen, Drugs for autoimmune inflammatory diseases: From small molecule compounds to anti-TNF biologics, Frontiers in Pharmacology. (2017). https://doi.org/10.3389/fphar.2017.00460.

[2] M. Sheth, C. M. Benedum, L. A. Celi, R. G. Mark, N. Markuzon, The association between autoimmune disease and 30-day mortality among sepsis ICU patients: A cohort study, Critical Care. (2019). https://doi.org/10.1186/s13054-019-2357-1.

[3] K. Migita, T. Arai, N. Ishizuka, Y. Jiuchi, Y. Sasaki, Y. Izumi, T. Kiyokawa, E. Suematsu, T. Miyamura, H. Tsutani, Y. Kawabe, R. Matsumura, S. Mori, S. Ohshima, S. Yoshizawa, K. Kawakami, Y. Suenaga, H. Nishimura, T. Sugimoto, H. Iwase, H. Sawada, H. Yamashita, S. Kuratsu, F. Ogushi, M. Kawabata, T. Matsui, H. Furukawa, S. Bito, S. Tohma, Rates of serious intracellular infections in autoimmune disease patients receiving initial glucocorticoid therapy, PLoS ONE. (2013). https://doi.org/10.1371/journal.pone.0078699.

[4] K. Hemminki, X. Liu, J. Ji, J. Sundquist, K. Sundquist, Autoimmune disease and subsequent digestive tract cancer by histology, Annals of Oncology. (2012). https://doi.org/10.1093/annonc/mdr333.

[5] A. L. Franks, J. E. Slansky, Multiple associations between a broad spectrum of autoimmune diseases, chronic inflammatory diseases, and cancer, Anticancer Research. (2012).

[6] K.-H. Yu, C.-F. Kuo, L. H. Huang, W.-K. Huang, L.-C. See, Cancer Risk in Patients With Inflammatory Systemic Autoimmune Rheumatic Diseases, Medicine. (2016). https://doi.org/10.1097/md.0000000000003540.

[7] A. Kornbluth, Infliximab Approved for Use in Crohn's Disease: A Report on the FDA GI Advisory Committee Conference, Inflammatory Bowel Diseases. (1998). https://doi.org/10.1097/00054725-199811000-00014.

[8] P. E. Lipsky, D. M. van der Heijde, E. W. St Clair, D. E. Furst, F. C. Breedveld, J. R. Kalden, J. S. Smolen, M. Weisman, P. Emery, M. Feldmann, G. R. Harriman, R. N. Maini, G. Anti-Tumor Necrosis Factor Trial in Rheumatoid Arthritis with Concomitant Therapy Study, Infliximab and methotrexate in the treatment of rheumatoid arthritis. Anti-Tumor Necrosis Factor Trial in Rheumatoid Arthritis with Concomitant Therapy Study Group.[see comment], New England Journal of Medicine. (2000).

[9] R. Maini, E. W. St Clair, F. Breedveld, D. Furst, J. Kalden, M. Weisman, J. Smolen, P. Emery, G. Harriman, M. Feldmann, P. Lipsky, Infliximab (chimeric anti-tumour necrosis factor α monoclonal antibody) versus placebo in rheumatoid arthritis patients receiving concomitant methotrexate: A randomised phase III trial, Lancet. (1999). https://doi.org/10.1016/S0140-6736(99)05246-0.

[10] G. Malviya, S. Salami, B. Laganà, A. P. Diamanti, R. D'Amelio, A. Signore, Biological therapies for rheumatoid arthritis: Progress to date, BioDrugs. (2013). https://doi.org/10.1007/s40259-013-0021-x.

[11] B. H. Hahn, M. A. McMahon, A. Wilkinson, W. D. Wallace, D. I. Daikh, J. D. Fitzgerald, G. A. Karpouzas, J. T. Merrill, D. J. Wallace, J. Yazdany, R. Ramsey-Goldman, K. Singh, M. Khalighi, S. I. Choi, M. Gogia, S. Kafaja, M. Kamgar, C. Lau, W. J. Martin, S. Parikh, J. Peng, A. Rastogi, W. Chen, J. M. Grossman, American College of Rheumatology guidelines for screening, treatment, and management of lupus nephritis, Arthritis Care and Research. (2012). https://doi.org/10.1002/acr.21664.

[12] J. Massagué, TGFbeta signalling in context, Nat Rev Mol Cell Biol. 13 (2014) 616-630. https://doi.org/10.1038/nrm3434.TGF.

[13] M. O. Li, Y. Y. Wan, R. A. Flavell, T Cell-Produced Transforming Growth Factor-β1 Controls T Cell Tolerance and Regulates Th1- and Th17-Cell Differentiation, *Immunity*. (2007). https://doi.org/10.1016/j.immuni.2007.03.014.
[14] J. Varga, B. Pasche, Transforming growth factor β as a therapeutic target in systemic sclerosis, Nature Reviews Rheumatology. (2009). https://doi.org/10.1038/nrrheum.2009.26.
[15] E. P. Bottinger, J. J. Letterio, A. B. Roberts, Biology of TGF-β in knockout and transgenic mouse models, Kidney International. (1997). https://doi.org/10.1038/ki.1997.185.
[16] X. J. Wang, D. A. Greenhalgh, J. R. Bickenbach, A. Jiang, D. S. Bundman, T. Krieg, R. Derynck, D. R. Roop, Expression of a dominant-negative type II transforming growth factor β (TGF-β) receptor in the epidermis of transgenic mice blocks TGF-β-mediated growth inhibition, Proceedings of the National Academy of Sciences of the United States of America. (1997). https://doi.org/10.1073/pnas.94.6.2386.
[17] E. P. Bottinger, J. L. Jakubczak, I. S. D. Roberts, M. Mumy, P. Hemmati, K. Bagnall, G. Merlino, L. M. Wakefield, Expression of a dominant-negative mutant TGF-β type II receptor in transgenic mice reveals essential roles for TGF-β in regulation of growth and differentiation in the exocrine pancreas, EMBO Journal. (1997). https://doi.org/10.1093/emboj/16.10.2621.
[18] R. Tinoco, V. Alcalde, Y. Yang, K. Sauer, E. I. Zuniga, Cell-Intrinsic Transforming Growth Factor-β Signaling Mediates Virus-Specific CD8+ T Cell Deletion and Viral Persistence In Vivo, *Immunity*. (2009). https://doi.org/10.1016/j.immuni.2009.06.015.
[19] S. Budhu, D. A. Schaer, Y. Li, R. Toledo-Crow, K. Panageas, X. Yang, H. Zhong, A. N. Houghton, S. C. Silverstein, T. Merghoub, J. D. Wolchok, Blockade of surface-bound TGF-β on regulatory T cells abrogates suppression of effector T cell function in the tumor microenvironment, Science Signaling. (2017). https://doi.org/10.1126/scisignal.aak9702.
[20] A. Śledzińska, S. Hemmers, F. Mair, O. Gorka, J. Ruland, L. Fairbairn, A. Nissler, W. Müller, A. Waisman, B. Becher, T. Buch, TGF-β Signalling Is Required for CD4+ T Cell Homeostasis But Dispensable for Regulatory T Cell Function, PLoS Biology. (2013). https://doi.org/10.1371/journal.pbio.1001674.
[21] M. J. Gros, P. Naquet, R. R. Guinamard, Cell Intrinsic TGF-β1 Regulation of B Cells, The Journal of Immunology. (2008). https://doi.org/10.4049/jimmunol.180.12.8153.
[22] A. M. MALYGIN, S. MERI, T. TIMONEN, Regulation of Natural Killer Cell Activity by Transforming Growth Factor-β and Prostaglandin E2, Scandinavian Journal of Immunology. (1993). https://doi.org/10.1111/j.1365-3083.1993.tb01667.x.
[23] L. Kubiczkova, L. Sedlarikova, R. Hajek, S. Sevcikova, TGF-β-an excellent servant but a bad master, Journal of Translational Medicine. (2012). https://doi.org/10.1186/1479-5876-10-183.
[24] DM Pardoll (March 2012). The blockade of immune checkpoints in cancer immunotherapy. Nature Reviews. Cancer. 12 (4): 252-64. doi:10.1038/nrc3239
[25] M. Sampedro-Núñez, A. Serrano-Somavilla, M. Adrados, J. M. Cameselle-Teijeiro, C. Blanco-Carrera, J. M. Cabezas-Agricola, R. Martinez-Hernández, E. Martin-Pérez, J. L. Muñoz de Nova, J. Á. Diaz, R. Garcia-Centeno, J. Caneiro-Gomez, I. Abdulkader, R. González-Amaro, M. Marazuela, Analysis of expression of the PD-1/PD-L1 immune checkpoint system and its prognostic impact in gastroenteropancreatic neuroendocrine tumors, Scientific Reports. 8 (2018) 1-11. https://doi.org/10.1038/s41598-018-36129-1.
[26] F. R. Mariotti, L. Quatrini, E. Munari, P. Vacca, L. Moretta, Innate lymphoid cells: Expression of PD-1 and other checkpoints in normal and pathological conditions, Frontiers in Immunology. (2019). https://doi.org/10.3389/fimmu.2019.00910.
[27] M. R. Zamani, S. Aslani, A. Salmaninejad, M. R. Javan, N. Rezaei, PD-1/PD-L, and autoimmunity: A growing relationship, *Cellular Immunology*. 310 (2016) 27-41. ttps://doi.org/10.1016/j.cellimm.2016.09.009.
[28] H. Nishimura, M. Nose, H. Hiai, N. Minato, T. Honjo, Development of lupus-like autoimmune diseases by disruption of the PD-1 gene encoding an ITIM motif-carrying immunoreceptor, *Immunity*. (1999). https://doi.org/10.1016/S1074-7613(00)80089-8.
[29] A. De Sousa Linhares, C. Battin, S. Jutz, J. Leitner, C. Hafner, J. Tobias, U. Wiedermann, M. Kundi, G. J. Zlabinger, K. Grabmeier-Pfistershammer, P. Steinberger, Therapeutic PD-L1 antibodies are more effective than PD-1 antibodies in blocking PD-1/PD-L1 signaling, Scientific Reports. 9 (2019) 1-9. https://doi.org/10.1038/s41598-019-47910-1.
[30] K. M. Mahoney, G. J. Freeman, D. F. McDermott, The next immune-checkpoint inhibitors: Pd-1/pd-I1 blockade in melanoma, Clinical Therapeutics. (2015). https://doi.org/10.1016/j.clinthera.2015.02.018.
[31] P Kolar, K Knieke, J K Hegel, D Quandt, G R Burmester, H Hoff, M C Brunner-Weinzierl (Jan. 1, 2009). "CTLA-4 (CD152) controls homeostasis and suppressive capacity of regulatory T cells in mice". *Arthritis Rheum.* 60 (1): 123-32. doi:10.1002/art.24181.
[32] N. C. Smits, C. L. Sentman, Bispecific T-cell engagers (BiTES) as treatment of B-cell lymphoma, Journal of Clinical Oncology. (2016). https://doi.org/10.1200/JCO.2015.64.9970.
[33] J. H. Esensten, Y. D. Muller, J. A. Bluestone, Q. Tang, Regulatory T-cell therapy for autoimmune and autoinflammatory diseases: The next frontier, Journal of Allergy, and Clinical Immunology. (2018). https://doi.org/10.1016/j.jaci.2018.10.015.
[34] M. Hagness, K. Henjum, J. Landskron, K. W. Brudvik, B. A. Bjørnbeth, A. Foss, K. Taskén, E. M. Aandahl, Kinetics and Activation Requirements of Contact-Dependent Immune Suppression by Human Regulatory T Cells, The Journal of Immunology. (2012). https://doi.org/10.4049/jimmunol.1101367.
[35] I Grenga, R N Donahue, M L Gargulak, L M Lepone, M Roselli, M Bilusic, J Schlom. Anti-PD-L1/TGFβR2 (M7824) fusion protein induces immunogenic modulation of human urothelial carcinoma cell lines, rendering them more susceptible to immune-mediated recognition and lysis. *J. Urol Oncol.* 2018 March;36(3):93.e1-93.e11. doi: 10.1016/j.urolonc.2017.09.027. Epub 2017 Nov. 2.PMID: 29103968
[36] Z Zhong, K D Carroll, D Policarpio, et al. Anti-transforming growth factor beta receptor II antibody has therapeutic efficacy against primary tumor growth and metastasis through multi-effects on cancer, stroma, and immune cells. Clin Cancer Res. 2010 Feb. 15; 16(4): 1191-205. doi: 10.1158/1078-0432.CCR-09-1634. Epub 2010 Feb. 9.PMID: 20145179.
[37] H Lind, S R Gameiro, C Jochems, et al. Dual targeting of TGF-β and PD-L1 via a bifunctional anti-PD-L1/TGF- βRII agent: status of preclinical and clinical advances. Immunother Cancer. 2020 Feb;8(1):e000433. doi: 10.1136/jitc-2019-000433.PMID: 32079617.

[38] A P Hinck et al, Transforming growth factor-beta 1: three-dimensional structure in solution and comparison with the X-ray structure of transforming growth factor-beta 2. (1996) *Biochemistry* 35, 8517-853.

[39] E Bathe and J Massagué. Transforming Grown Factor-β Signaling in Immunity and Cancer. *Immunity.* 2019 Apr. 16; 50(4): 924-940. doi:10.1016/j.immuni.2019.03.024.

We claim in this invention:

1. A fusion protein comprising (i) a Transforming Growth Factor—Beta (TGF-B) ligand, wherein the TGF-B consists of TGF-B1 (SEQ ID NO: 14), linked by a rigid peptide linker (SEQ ID NO: 27) to (ii) an immune checkpoint ligand, wherein the immune checkpoint ligand consists of PD-L1 (SEQ ID NO: 17); and wherein the TGF-B1 ligand and immune checkpoint PD-L1 ligands are capable of binding to TGF-B receptors and immune checkpoint receptors, respectively, that are expressed in human and animal cells.

2. The fusion protein as recited in claim 1, wherein the TGF-B ligand is constructed by two TGF-B1 domains, linked by a flexible peptide linker (SEQ ID NO: 20) resulting in Homo-Dimeric TGF-B1 ligand (SEQ ID NO: 21).

3. A dimeric TGF-B ligand wherein the TGF-B ligand is constructed by two TGF-B1 domains, linked by a flexible peptide linker (SEQ ID NO: 20) resulting in Homo-Dimeric TGF-B1 (SEQ ID NO: 21), wherein the dimeric TGF-B1 ligand can bind to TGF-B receptors in human and animal cells.

4. The fusion protein as recited in claim 1, wherein the fusion protein is linked to an antibody, Fab fragment or cellular antigen-binding domain that binds to receptors of immune cellular antigens and tumor-associated antigens.

5. The fusion protein as recited in claim 2, wherein the fusion protein is linked to an antibody, Fab fragment or cellular antigen-binding domain that binds to receptors of immune cellular antigens and tumor-associated antigens.

6. The dimeric TGF-B ligand as recited in claim 3, wherein the dimeric TGF-B ligand is linked to a construct linked to an antibody, Fab fragment or cellular antigen domain that binds to receptors of immune cellular antigens and tumor-associated antigens.

7. The fusion protein as recited in claim 1 and a carrier.

8. The fusion protein as recited in claim 2 and a carrier.

9. The dimeric TGF-B ligand as recited in claim 3 and a carrier.

10. The dimeric TGF-B ligand construct as recited in claim 6 and a carrier.

* * * * *

```
                              SEQUENCE LISTING

<160> NUMBER OF SEQ ID NOS: 49

<210> SEQ ID NO 1
<211> LENGTH: 1422
<212> TYPE: DNA
<213> ORGANISM: Homo sapiens

<400> SEQUENCE: 1
atggccctgg acaccaacta ttgcttcagc tccacggaga agaactgctg cgtgcggcag      60
ctgtacattg acttccgcaa ggacctcggc tggaagtgga tccacgagcc caagggctac    120
catgccaact tctgcctcgg ccctgcccc tacatttgga gcctggacac gcagtacagc     180
aaggtcctgg ccctgtacaa ccagcataac ccgggcgcct cggcggcgcc gtgctgcgtg    240
ccgcaggcgc tggagccgct gcccatcgtg tactacgtgg gccgcaagcc caaggtggag    300
cagctgtcca acatgatcgt gcgctcctgc aagtgcagcg gtggaggcgg tagcggtgga    360
ggcggtagcg gtggaggcgg tagcatggcc ctggacacca actattgctt cagctccacg    420
gagaagaact gctgcgtgcg gcagctgtac attgacttcc gcaaggacct cggctggaag    480
tggatccacg agcccaaggg ctaccatgcc aacttctgcc tcgggccctg ccctacatt    540 tggagcctgg acacgcagta cagcaaggtc ctggccctgt acaaccagca taacccgggc    600
gcctcggcgc gccgtgctg cgtgccgcag gcgctggagc cgctgcccat cgtgtactac    660
gtgggccgca agcccaaggt ggagcagctg tccaacatga tcgtgcgctc ctgcaagtgc    720
agcgcggaag cggcggcgaa agaagcggcg gcgaaagcgt ttactgtcac ggttcccaag    780
gacctatatg tggtagagta tggtagcaat atgacaattg aatgcaaatt cccagtagaa    840
aaacaattag acctggctgc actaattgtc tattgggaaa tggaggataa gaacattatt    900
caatttgtgc atggagagga agacctgaag gttcagcata gtagctacag acagagggcc    960
cggctgttga aggaccagct ctccctggga aatgctgcac ttcagatcac agatgtgaaa   1020
ttgcaggatg cagggtgta ccgctgcatg atcagctatg gtggtgccga ctacaagcga   1080
attactgtga aagtcaatgc cccatacaac aaaatcaacc aaagaatttt ggttgtggat   1140
ccagtcacct ctgaacatga actgacatgt caggctgagg ctaccccaa ggccgaagtc   1200 atctggacaa gcagtgacca tcaagtcctg agtggtaaga ccaccaccac caattccaag   1260
agagaggaga agcttttcaa tgtgaccagc acactgagaa tcaacacaac aactaatgag   1320 atttttctact gcacttttag gagattagat cctgaggaaa accatacagc tgaattggtc   1380
atcccagaac tacctctggc acatcctcca aatgaaaggt ga                       1422

<210> SEQ ID NO 2
<211> LENGTH: 339
<212> TYPE: DNA
<213> ORGANISM: Homo sapiens

<400> SEQUENCE: 2
atggccctgg acaccaacta ttgcttcagc tccacggaga agaactgctg cgtgcggcag      60
ctgtacattg acttccgcaa ggacctcggc tggaagtgga tccacgagcc caagggctac    120
catgccaact tctgcctcgg ccctgcccc tacatttgga gcctggacac gcagtacagc     180
```

| | |
|---|---:|
| aaggtcctgg ccctgtacaa ccagcataac ccgggcgcct cggcggcgcc gtgctgcgtg | 240 |
| ccgcaggcgc tggagccgct gcccatcgtg tactacgtgg gccgcaagcc caaggtggag | 300 |
| cagctgtcca acatgatcgt gcgctcctgc aagtgcagc | 339 |

<210> SEQ ID NO 3
<211> LENGTH: 339
<212> TYPE: DNA
<213> ORGANISM: Homo sapiens

<400> SEQUENCE: 3

| | |
|---|---:|
| atggctttgg atgcggccta ttgctttaga aatgtgcagg ataattgctg cctacgtcca | 60 |
| ctttacattg atttcaagag ggatctaggg tggaaatgga tacacgaacc caagggtac | 120 |
| aatgccaact tctgtgctgg agcatgcccg tatttatgga gttcagacac tcagcacagc | 180 |
| agggtcctga gcttatataa taccataaat ccagaagcat ctgcttctcc ttgctgcgtg | 240 |
| tcccaagatt tagaacctct aaccattctc tactacattg gcaaaacacc caagattgaa | 300 |
| cagctttcta atatgattgt aaagtcttgc aaatgcagc | 339 |

<210> SEQ ID NO 4
<211> LENGTH: 339
<212> TYPE: DNA
<213> ORGANISM: Homo sapiens

<400> SEQUENCE: 4

| | |
|---|---:|
| atggctttgg acaccaatta ctgcttccgc aacttggagg agaactgctg tgtgcgcccc | 60 |
| ctctacattg acttccgaca ggatctgggc tggaagtggg tccatgaacc taagggctac | 120 |
| tatgccaact tctgctcagg cccttgccca tacctccgca gtgcagacac aacccacagc | 180 |
| acggtgctgg gactgtacaa cactctgaac cctgaagcat ctgcctcgcc ttgctgcgtg | 240 |
| ccccaggacc tggagcccct gaccatcctg tactatgttg ggaggacccc caaagtggag | 300 |
| cagctctcca acatggtggt gaagtcttgt aaatgtagc | 339 |

<210> SEQ ID NO 5
<211> LENGTH: 45
<212> TYPE: DNA
<213> ORGANISM: Homo sapiens

<400> SEQUENCE: 5

| | |
|---|---:|
| ggtggaggcg gtagcggtgg aggcggtagc ggtggaggcg gtagc | 45 |

<210> SEQ ID NO 6
<211> LENGTH: 663
<212> TYPE: DNA
<213> ORGANISM: Homo sapiens

<400> SEQUENCE: 6

| | |
|---|---:|
| tttactgtca cggttcccaa ggacctatat gtggtagagt atggtagcaa tatgacaatt | 60 |
| gaatgcaaat tcccagtaga aaacaattg gacctggctg cactaattgt ctattgggaa | 120 |
| atggaggata agaacattat tcaatttgtg catggagagg aagacctgaa ggttcagcat | 180 |
| agtagctaca cagagagggc ccggctgttg aaggaccagc tctccctggg aaatgctgca | 240 |
| cttcagatca cagatgtgaa attgcaggat gcaggggtgt accgctgcat gatcagctat | 300 |
| ggtggtgccg actacaagcg aattactgtg aaagtcaatg ccccatacaa caaaatcaac | 360 |
| caaagaattt tggttgtgga tccagtcacc tctgaacatg aactgacatg tcaggctgag | 420 |
| ggctacccca aggccgaagt catctggaca agcagtgacc atcaagtcct gagtggtaag | 480 |

| | |
|---|---|
| accaccacca ccaattccaa gagagaggag aagcttttca atgtgaccag cacactgaga | 540 |
| atcaacacaa caactaatga gatttttctac tgcacttttta ggagattaga tcctgaggaa | 600 |
| aaccatacag ctgaattggt catcccagaa ctacctctgg cacatcctcc aaatgaaagg | 660 |
| tga | 663 |

<210> SEQ ID NO 7
<211> LENGTH: 606
<212> TYPE: DNA
<213> ORGANISM: Homo sapiens

<400> SEQUENCE: 7

| | |
|---|---|
| ttattcacag tgacagtccc taaggaactg tacataatag agcatggcag caatgtgacc | 60 |
| ctggaatgca actttgacac tggaagtcat gtgaaccttg gagcaataac agccagtttg | 120 |
| caaaaggtgg aaaatgatac atccccacac cgtgaaagag ccactttgct ggaggagcag | 180 |
| ctgcccctag gaaggcctc gttccacata cctcaagtcc aagtgaggga cgaaggacag | 240 |
| taccaatgca taatcatcta tgggtcgcc tgggactaca agtacctgac tctgaaagtc | 300 |
| aaagcttcct acaggaaaat aaacactcac atcctaaagg ttccagaaac agatgaggta | 360 |
| gagctcacct gccaggctac aggttatcct ctggcagaag tatcctggcc aaacgtcagc | 420 |
| gttcctgcca acaccagcca ctccaggacc cctgaaggcc tctaccaggt caccagtgtt | 480 |
| ctgcgcctaa agccaccccc tggcagaaac ttcagctgtg tgttctggaa tactcacgtg | 540 |
| agggaactta ctttggccag cattgacctt caaagtcaga tggaacccag gacccatcca | 600 |
| acttga | 606 |

<210> SEQ ID NO 8
<211> LENGTH: 381
<212> TYPE: DNA
<213> ORGANISM: Homo sapiens

<400> SEQUENCE: 8

| | |
|---|---|
| aaagcaatgc acgtggccca gcctgctgtg gtactggcca gcagccgagg catcgccagc | 60 |
| tttgtgtgtg agtatgcatc tccaggcaaa gccactgagg tccgggtgac agtgcttcgg | 120 |
| caggctgaca gccaggtgac tgaagtctgt gcggcaacct acatgatggg gaatgagttg | 180 |
| accttcctag atgattccat ctgcacgggc acctccagtg gaaatcaagt gaacctcact | 240 |
| atccaaggac tgagggccat ggacacggga ctctacatct gcaaggtgga gctcatgtac | 300 |
| ccaccgccat actacctggg cataggcaac ggaacccaga tttatgtaat tgatccagaa | 360 |
| ccgtgcccag attctgactg a | 381 |

<210> SEQ ID NO 9
<211> LENGTH: 723
<212> TYPE: DNA
<213> ORGANISM: Homo sapiens

<400> SEQUENCE: 9

| | |
|---|---|
| atggccctgg acaccaacta ttgcttcagc tccacggaga agaactgctg cgtgcggcag | 60 |
| ctgtacattg acttccgcaa ggacctcggc tggaagtgga tccacgagcc aagggctac | 120 |
| catgccaact tctgcctcgg gccctgcccc tacatttgga gcctggacac gcagtacagc | 180 |
| aaggtcctgg ccctgtacaa ccagcataac ccgggcgcct cggcggcgcc gtgctgcgtg | 240 |
| ccgcaggcgc tggagccgct gcccatcgtg tactacgtgg gccgcaagcc caaggtggag | 300 |
| cagctgtcca acatgatcgt gcgctcctgc aagtgcagcg gtggaggcgg tagcggtgga | 360 |

```
ggcggtagcg gtggaggcgg tagcatggcc ctggacacca actattgctt cagctccacg    420
gagaagaact gctgcgtgcg gcagctgtac attgacttcc gcaaggacct cggctggaag    480
tggatccacg agcccaaggg ctaccatgcc aacttctgcc tcgggccctg ccctacatt     540 tggagcctgg acacgcagta cagcaaggtc ctggccctgt acaaccagca taacccgggc    600
gcctcggcgg cgccgtgctg cgtgccgcag gcgctggagc cgctgcccat cgtgtactac    660
gtgggccgca agcccaaggt ggagcagctg tccaacatga tcgtgcgctc ctgcaagtgc    720
agc                                                                  723
```

```
<210> SEQ ID NO 10
<211> LENGTH: 720
<212> TYPE: DNA
<213> ORGANISM: Homo sapiens

<400> SEQUENCE: 10
atggctttgg atgcggccta ttgctttaga aatgtgcagg ataattgctg cctacgtcca     60 cttacattg atttcaagag ggatctaggg tggaaatgga tacacgaacc caagggtac    120 aatgccaact tctgtgctgg agcatgcccg tatttatgga gttcagacac tcagcacagc    180
agggtcctga gcttatataa taccataaat ccagaagcat ctgcttctcc ttgctgcgtg    240
tcccaagatt tagaacctct aaccattctc tactacattg gcaaaacacc caagattgaa    300 cagcttctcta atatgattgt aaagtcttgc aaatgcagcg tggaggcgg tagcggtgga    360 ggcggtagcg gtggaggcgg tagcgctttg gatgcggcct attgctttag aaatgtgcag    420
gataattgct gcctacgtcc actttacatt gatttcaaga gggatctagg gtggaaatgg    480
atacacgaac ccaaggtta caatgccaac ttctgtgctg gagcatgccc gtatttatgg    540
agttcagaca ctcagcacag cagggtcctg agcttatata taccataaa tccagaagca    600 tctgcttctc cttgctgcgt gtcccaagat ttagaacctc taaccattct ctactacatt    660
ggcaaaacac ccaagattga acagctttct aatatgattg taaagtcttg caaatgcagc    720
```

```
<210> SEQ ID NO 11
<211> LENGTH: 720
<212> TYPE: DNA
<213> ORGANISM: Homo sapiens

<400> SEQUENCE: 11
atggctttgg acaccaatta ctgcttccgc aacttggagg agaactgctg tgtgcgcccc     60
ctctacattg acttccgaca ggatctgggc tggaagtggg tccatgaacc taagggctac    120
tatgccaact tctgctcagg cccttgccca tacctccgca gtgcagacac aacccacagc    180
acggtgctgg gactgtacaa cactctgaac cctgaagcat ctgcctcgcc ttgctgcgtg    240
ccccaggacc tggagcccct gaccatcctg tactatgttg gaggacccc caaagtggag    300 cagctctcca catggtggt gaagtcttgt aaatgtagcg tggaggcgg tagcggtgga    360 ggcggtagcg gtggaggcgg tagcgctttg gacaccaatt actgcttccg caacttggag    420
gagaactgct gtgtgcgccc cctctacatt gacttccgac aggatctggg ctggaagtgg    480
gtccatgaac ctaagggcta ctatgccaac ttctgctcag gccctttgccc ataccctccgc    540 agtgcagaca caacccacag cacggtgctg ggactgtaca acactctgaa ccctgaagca    600
tctgcctcgc cttgctgcgt gccccaggac ctggagcccc tgaccatcct gtactatgtt    660
gggaggaccc ccaaagtgga gcagctctcc aacatggtgg tgaagtcttg taaatgtagc    720
```

<210> SEQ ID NO 12
<211> LENGTH: 36
<212> TYPE: DNA
<213> ORGANISM: Homo sapiens

<400> SEQUENCE: 12
gcggaagcgg cggcgaaaga agcggcggcg aaagcg          36

<210> SEQ ID NO 13
<211> LENGTH: 473
<212> TYPE: PRT
<213> ORGANISM: Homo sapiens

<400> SEQUENCE: 13

```
Met Ala Leu Asp Thr Asn Tyr Cys Phe Ser Ser Thr Glu Lys Asn Cys
1               5                   10                  15

Cys Val Arg Gln Leu Tyr Ile Asp Phe Arg Lys Asp Leu Gly Trp Lys
            20                  25                  30

Trp Ile His Glu Pro Lys Gly Tyr His Ala Asn Phe Cys Leu Gly Pro
        35                  40                  45

Cys Pro Tyr Ile Trp Ser Leu Asp Thr Gln Tyr Ser Lys Val Leu Ala
    50                  55                  60

Leu Tyr Asn Gln His Asn Pro Gly Ala Ser Ala Ala Pro Cys Cys Val
65                  70                  75                  80

Pro Gln Ala Leu Glu Pro Leu Pro Ile Val Tyr Tyr Val Gly Arg Lys
                85                  90                  95

Pro Lys Val Glu Gln Leu Ser Asn Met Ile Val Arg Ser Cys Lys Cys
            100                 105                 110

Ser Gly Gly Gly Gly Ser Gly Gly Gly Ser Gly Gly Gly Gly Ser
        115                 120                 125

Met Ala Leu Asp Thr Asn Tyr Cys Phe Ser Ser Thr Glu Lys Asn Cys
    130                 135                 140

Cys Val Arg Gln Leu Tyr Ile Asp Phe Arg Lys Asp Leu Gly Trp Lys
145                 150                 155                 160

Trp Ile His Glu Pro Lys Gly Tyr His Ala Asn Phe Cys Leu Gly Pro
                165                 170                 175

Cys Pro Tyr Ile Trp Ser Leu Asp Thr Gln Tyr Ser Lys Val Leu Ala
            180                 185                 190

Leu Tyr Asn Gln His Asn Pro Gly Ala Ser Ala Ala Pro Cys Cys Val
        195                 200                 205

Pro Gln Ala Leu Glu Pro Leu Pro Ile Val Tyr Tyr Val Gly Arg Lys
    210                 215                 220

Pro Lys Val Glu Gln Leu Ser Asn Met Ile Val Arg Ser Cys Lys Cys
225                 230                 235                 240

Ser Ala Glu Ala Ala Ala Lys Glu Ala Ala Lys Ala Phe Thr Val
                245                 250                 255

Thr Val Pro Lys Asp Leu Tyr Val Val Glu Tyr Gly Ser Asn Met Thr
            260                 265                 270

Ile Glu Cys Lys Phe Pro Val Glu Lys Gln Leu Asp Leu Ala Ala Leu
        275                 280                 285

Ile Val Tyr Trp Glu Met Glu Asp Lys Asn Ile Ile Gln Phe Val His
    290                 295                 300

Gly Glu Glu Asp Leu Lys Val Gln His Ser Ser Tyr Arg Gln Arg Ala
305                 310                 315                 320

Arg Leu Leu Lys Asp Gln Leu Ser Leu Gly Asn Ala Ala Leu Gln Ile
                325                 330                 335
```

```
Thr Asp Val Lys Leu Gln Asp Ala Gly Val Tyr Arg Cys Met Ile Ser
            340                 345                 350

Tyr Gly Gly Ala Asp Tyr Lys Arg Ile Thr Val Lys Val Asn Ala Pro
        355                 360                 365

Tyr Asn Lys Ile Asn Gln Arg Ile Leu Val Val Asp Pro Val Thr Ser
370                 375                 380

Glu His Glu Leu Thr Cys Gln Ala Glu Gly Tyr Pro Lys Ala Glu Val
385                 390                 395                 400

Ile Trp Thr Ser Ser Asp His Gln Val Leu Ser Gly Lys Thr Thr Thr
                405                 410                 415

Thr Asn Ser Lys Arg Glu Glu Lys Leu Phe Asn Val Thr Ser Thr Leu
            420                 425                 430

Arg Ile Asn Thr Thr Thr Asn Glu Ile Phe Tyr Cys Thr Phe Arg Arg
            435                 440                 445

Leu Asp Pro Glu Glu Asn His Thr Ala Glu Leu Val Ile Pro Glu Leu
        450                 455                 460

Pro Leu Ala His Pro Pro Asn Glu Arg
465                 470

<210> SEQ ID NO 14
<211> LENGTH: 113
<212> TYPE: PRT
<213> ORGANISM: Homo sapiens

<400> SEQUENCE: 14

Met Ala Leu Asp Thr Asn Tyr Cys Phe Ser Ser Thr Glu Lys Asn Cys
1               5                   10                  15

Cys Val Arg Gln Leu Tyr Ile Asp Phe Arg Lys Asp Leu Gly Trp Lys
            20                  25                  30

Trp Ile His Glu Pro Lys Gly Tyr His Ala Asn Phe Cys Leu Gly Pro
        35                  40                  45

Cys Pro Tyr Ile Trp Ser Leu Asp Thr Gln Tyr Ser Lys Val Leu Ala
    50                  55                  60

Leu Tyr Asn Gln His Asn Pro Gly Ala Ser Ala Ala Pro Cys Cys Val
65                  70                  75                  80

Pro Gln Ala Leu Glu Pro Leu Pro Ile Val Tyr Tyr Val Gly Arg Lys
                85                  90                  95

Pro Lys Val Glu Gln Leu Ser Asn Met Ile Val Arg Ser Cys Lys Cys
            100                 105                 110

Ser

<210> SEQ ID NO 15
<211> LENGTH: 113
<212> TYPE: PRT
<213> ORGANISM: Homo sapiens

<400> SEQUENCE: 15

Met Ala Leu Asp Ala Ala Tyr Cys Phe Arg Asn Val Gln Asp Asn Cys
1               5                   10                  15

Cys Leu Arg Pro Leu Tyr Ile Asp Phe Lys Arg Asp Leu Gly Trp Lys
            20                  25                  30

Trp Ile His Glu Pro Lys Gly Tyr Asn Ala Asn Phe Cys Ala Gly Ala
        35                  40                  45

Cys Pro Tyr Leu Trp Ser Ser Asp Thr Gln His Ser Arg Val Leu Ser
    50                  55                  60
```

```
Leu Tyr Asn Thr Ile Asn Pro Glu Ala Ser Ala Ser Pro Cys Cys Val
 65                  70                  75                  80

Ser Gln Asp Leu Glu Pro Leu Thr Ile Leu Tyr Tyr Ile Gly Lys Thr
                 85                  90                  95

Pro Lys Ile Glu Gln Leu Ser Asn Met Ile Val Lys Ser Cys Lys Cys
                100                 105                 110

Ser

<210> SEQ ID NO 16
<211> LENGTH: 113
<212> TYPE: PRT
<213> ORGANISM: Homo sapiens

<400> SEQUENCE: 16

Met Ala Leu Asp Thr Asn Tyr Cys Phe Arg Asn Leu Glu Glu Asn Cys
  1               5                  10                  15

Cys Val Arg Pro Leu Tyr Ile Asp Phe Arg Gln Asp Leu Gly Trp Lys
                 20                  25                  30

Trp Val His Glu Pro Lys Gly Tyr Tyr Ala Asn Phe Cys Ser Gly Pro
             35                  40                  45

Cys Pro Tyr Leu Arg Ser Ala Asp Thr Thr His Ser Thr Val Leu Gly
 50                  55                  60

Leu Tyr Asn Thr Leu Asn Pro Glu Ala Ser Ala Ser Pro Cys Cys Val
 65                  70                  75                  80

Pro Gln Asp Leu Glu Pro Leu Thr Ile Leu Tyr Tyr Val Gly Arg Thr
                 85                  90                  95

Pro Lys Val Glu Gln Leu Ser Asn Met Val Val Lys Ser Cys Lys Cys
                100                 105                 110

Ser

<210> SEQ ID NO 17
<211> LENGTH: 221
<212> TYPE: PRT
<213> ORGANISM: Homo sapiens

<400> SEQUENCE: 17

Phe Thr Val Thr Val Pro Lys Asp Leu Tyr Val Val Glu Tyr Gly Ser
  1               5                  10                  15

Asn Lys Met Thr Ile Glu Cys Lys Phe Pro Val Glu Lys Gln Leu Asp
                 20                  25                  30

Leu Ala Ala Leu Ile Val Tyr Trp Glu Met Glu Asp Lys Asn Ile Ile
             35                  40                  45

Gln Phe Val His Gly Glu Glu Asp Leu Lys Val Gln His Ser Ser Tyr
 50                  55                  60

Arg Gln Arg Ala Arg Leu Leu Lys Asp Gln Leu Ser Leu Gly Asn Ala
 65                  70                  75                  80

Ala Leu Gln Ile Thr Asp Val Lys Leu Gln Asp Ala Gly Val Tyr Arg
                 85                  90                  95

Cys Met Ile Ser Tyr Gly Gly Ala Asp Tyr Lys Arg Ile Thr Val Lys
                100                 105                 110

Val Asn Ala Pro Tyr Asn Lys Ile Asn Gln Arg Ile Leu Val Val Asp
            115                 120                 125

Pro Val Thr Ser Glu His Glu Leu Thr Cys Gln Ala Glu Gly Tyr Pro
130                 135                 140

Lys Ala Glu Val Ile Trp Thr Ser Ser Asp His Gln Val Leu Ser Gly
145                 150                 155                 160
```

```
Lys Thr Thr Thr Thr Asn Ser Lys Arg Glu Glu Lys Leu Phe Asn Val
                165                 170                 175

Thr Ser Thr Leu Arg Ile Asn Thr Thr Asn Glu Ile Phe Tyr Cys
            180                 185                 190

Thr Phe Arg Arg Leu Asp Pro Glu Glu Asn His Thr Ala Glu Leu Val
            195                 200                 205

Ile Pro Glu Leu Pro Leu Ala His Pro Pro Asn Glu Arg
210                 215                 220
```

<210> SEQ ID NO 18
<211> LENGTH: 201
<212> TYPE: PRT
<213> ORGANISM: Homo sapiens

<400> SEQUENCE: 18

```
Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr
        195                 200
```

<210> SEQ ID NO 19
<211> LENGTH: 126
<212> TYPE: PRT
<213> ORGANISM: Homo sapiens

<400> SEQUENCE: 19

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60
```

```
Asp Ser Ile Cys Thr Gly Thr Ser Ser Gly Asn Gln Val Asn Leu Thr
 65                  70                  75                  80

Ile Gln Gly Leu Arg Ala Met Asp Thr Gly Leu Tyr Ile Cys Lys Val
                 85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125

<210> SEQ ID NO 20
<211> LENGTH: 15
<212> TYPE: PRT
<213> ORGANISM: Homo sapiens

<400> SEQUENCE: 20

Gly Gly Gly Gly Ser Gly Gly Gly Gly Ser Gly Gly Gly Gly Ser
  1               5                  10                  15

<210> SEQ ID NO 21
<211> LENGTH: 241
<212> TYPE: PRT
<213> ORGANISM: Homo sapiens

<400> SEQUENCE: 21

Met Ala Leu Asp Thr Asn Tyr Cys Phe Ser Ser Thr Glu Lys Asn Cys
  1               5                  10                  15

Cys Val Arg Gln Leu Tyr Ile Asp Phe Arg Lys Asp Leu Gly Trp Lys
                 20                  25                  30

Trp Ile His Glu Pro Lys Gly Tyr His Ala Asn Phe Cys Leu Gly Pro
             35                  40                  45

Cys Pro Tyr Ile Trp Ser Leu Asp Thr Gln Tyr Ser Lys Val Leu Ala
 50                  55                  60

Leu Tyr Asn Gln His Asn Pro Gly Ala Ser Ala Ala Pro Cys Cys Val
 65                  70                  75                  80

Pro Gln Ala Leu Glu Pro Leu Pro Ile Val Tyr Tyr Val Gly Arg Lys
                 85                  90                  95

Pro Lys Val Glu Gln Leu Ser Asn Met Ile Val Arg Ser Cys Lys Cys
            100                 105                 110

Ser Gly Gly Gly Gly Ser Gly Gly Gly Gly Ser Gly Gly Gly Gly Ser
            115                 120                 125

Met Ala Leu Asp Thr Asn Tyr Cys Phe Ser Ser Thr Glu Lys Asn Cys
130                 135                 140

Cys Val Arg Gln Leu Tyr Ile Asp Phe Arg Lys Asp Leu Gly Trp Lys
145                 150                 155                 160

Trp Ile His Glu Pro Lys Gly Tyr His Ala Asn Phe Cys Leu Gly Pro
                165                 170                 175

Cys Pro Tyr Ile Trp Ser Leu Asp Thr Gln Tyr Ser Lys Val Leu Ala
            180                 185                 190

Leu Tyr Asn Gln His Asn Pro Gly Ala Ser Ala Ala Pro Cys Cys Val
        195                 200                 205

Pro Gln Ala Leu Glu Pro Leu Pro Ile Val Tyr Tyr Val Gly Arg Lys
    210                 215                 220

Pro Lys Val Glu Gln Leu Ser Asn Met Ile Val Arg Ser Cys Lys Cys
225                 230                 235                 240

Ser
```

```
<210> SEQ ID NO 22
<211> LENGTH: 240
<212> TYPE: PRT
<213> ORGANISM: Homo sapiens

<400> SEQUENCE: 22

Met Ala Leu Asp Thr Asn Tyr Cys Phe Ser Ser Thr Glu Lys Asn Cys
1               5                   10                  15

Cys Val Arg Gln Leu Tyr Ile Asp Phe Arg Lys Asp Leu Gly Trp Lys
                20                  25                  30

Trp Ile His Glu Pro Lys Gly Tyr His Ala Asn Phe Cys Leu Gly Pro
            35                  40                  45

Cys Pro Tyr Ile Trp Ser Leu Asp Thr Gln Tyr Ser Lys Val Leu Ala
50                  55                  60

Leu Tyr Asn Gln His Asn Pro Gly Ala Ser Ala Ala Pro Cys Cys Val
65                  70                  75                  80

Pro Gln Ala Leu Glu Pro Leu Pro Ile Val Tyr Tyr Val Gly Arg Lys
                85                  90                  95

Pro Lys Val Glu Gln Leu Ser Asn Met Ile Val Arg Ser Cys Lys Cys
            100                 105                 110

Ser Gly Gly Gly Gly Ser Gly Gly Gly Ser Gly Gly Gly Gly Ser
            115                 120                 125

Ala Leu Asp Ala Ala Tyr Cys Phe Arg Asn Val Gln Asp Asn Cys Cys
        130                 135                 140

Leu Arg Pro Leu Tyr Ile Asp Phe Lys Arg Asp Leu Gly Trp Lys Trp
145                 150                 155                 160

Ile His Glu Pro Lys Gly Tyr Asn Ala Asn Phe Cys Ala Gly Ala Cys
                165                 170                 175

Pro Tyr Leu Trp Ser Ser Asp Thr Gln His Ser Arg Val Leu Ser Leu
            180                 185                 190

Tyr Asn Thr Ile Asn Pro Glu Ala Ser Ala Ser Pro Cys Cys Val Ser
        195                 200                 205

Gln Asp Leu Glu Pro Leu Thr Ile Leu Tyr Tyr Ile Gly Lys Thr Pro
210                 215                 220

Lys Ile Glu Gln Leu Ser Asn Met Ile Val Lys Ser Cys Lys Cys Ser
225                 230                 235                 240

<210> SEQ ID NO 23
<211> LENGTH: 240
<212> TYPE: PRT
<213> ORGANISM: Homo sapiens

<400> SEQUENCE: 23

Met Ala Leu Asp Thr Asn Tyr Cys Phe Ser Ser Thr Glu Lys Asn Cys
1               5                   10                  15

Cys Val Arg Gln Leu Tyr Ile Asp Phe Arg Lys Asp Leu Gly Trp Lys
                20                  25                  30

Trp Ile His Glu Pro Lys Gly Tyr His Ala Asn Phe Cys Leu Gly Pro
            35                  40                  45

Cys Pro Tyr Ile Trp Ser Leu Asp Thr Gln Tyr Ser Lys Val Leu Ala
50                  55                  60

Leu Tyr Asn Gln His Asn Pro Gly Ala Ser Ala Ala Pro Cys Cys Val
65                  70                  75                  80

Pro Gln Ala Leu Glu Pro Leu Pro Ile Val Tyr Tyr Val Gly Arg Lys
                85                  90                  95
```

```
Pro Lys Val Glu Gln Leu Ser Asn Met Ile Val Arg Ser Cys Lys Cys
            100                 105                 110

Ser Gly Gly Gly Gly Ser Gly Gly Gly Ser Gly Gly Gly Ser
        115                 120                 125

Ala Leu Asp Thr Asn Tyr Cys Phe Arg Asn Leu Glu Glu Asn Cys Cys
    130                 135                 140

Val Arg Pro Leu Tyr Ile Asp Phe Arg Gln Asp Leu Gly Trp Lys Trp
145                 150                 155                 160

Val His Glu Pro Lys Gly Tyr Tyr Ala Asn Phe Cys Ser Gly Pro Cys
                165                 170                 175

Pro Tyr Leu Arg Ser Ala Asp Thr Thr His Ser Thr Val Leu Gly Leu
            180                 185                 190

Tyr Asn Thr Leu Asn Pro Glu Ala Ser Ala Ser Pro Cys Cys Val Pro
    195                 200                 205

Gln Asp Leu Glu Pro Leu Thr Ile Leu Tyr Tyr Val Gly Arg Thr Pro
            210                 215                 220

Lys Val Glu Gln Leu Ser Asn Met Val Val Lys Ser Cys Lys Cys Ser
225                 230                 235                 240

<210> SEQ ID NO 24
<211> LENGTH: 239
<212> TYPE: PRT
<213> ORGANISM: Homo sapiens

<400> SEQUENCE: 24

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

Gly Gly Gly Gly Ser Gly Gly Gly Ser Gly Gly Gly Ser Ala
        115                 120                 125

Leu Asp Ala Ala Tyr Cys Phe Arg Asn Val Gln Asp Asn Cys Cys Leu
    130                 135                 140

Arg Pro Leu Tyr Ile Asp Phe Lys Arg Asp Leu Gly Trp Lys Trp Ile
145                 150                 155                 160

His Glu Pro Lys Gly Tyr Asn Ala Asn Phe Cys Ala Gly Ala Cys Pro
                165                 170                 175

Tyr Leu Trp Ser Ser Asp Thr Gln His Ser Arg Val Leu Ser Leu Tyr
            180                 185                 190

Asn Thr Ile Asn Pro Glu Ala Ser Ala Ser Pro Cys Cys Val Ser Gln
    195                 200                 205

Asp Leu Glu Pro Leu Thr Ile Leu Tyr Tyr Ile Gly Lys Thr Pro Lys
210                 215                 220

Ile Glu Gln Leu Ser Asn Met Ile Val Lys Ser Cys Lys Cys Ser
225                 230                 235
```

```
<210> SEQ ID NO 25
<211> LENGTH: 239
<212> TYPE: PRT
<213> ORGANISM: Homo sapiens

<400> SEQUENCE: 25

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

Gly Gly Gly Gly Ser Gly Gly Gly Ser Gly Gly Gly Gly Ser Ala
        115                 120                 125

Leu Asp Thr Asn Tyr Cys Phe Arg Asn Leu Glu Glu Asn Cys Cys Val
    130                 135                 140

Arg Pro Leu Tyr Ile Asp Phe Arg Gln Asp Leu Gly Trp Lys Trp Val
145                 150                 155                 160

His Glu Pro Lys Gly Tyr Tyr Ala Asn Phe Cys Ser Gly Pro Cys Pro
                165                 170                 175

Tyr Leu Arg Ser Ala Asp Thr Thr His Ser Thr Val Leu Gly Leu Tyr
            180                 185                 190

Asn Thr Leu Asn Pro Glu Ala Ser Ala Ser Pro Cys Cys Val Pro Gln
        195                 200                 205

Asp Leu Glu Pro Leu Thr Ile Leu Tyr Tyr Val Gly Arg Thr Pro Lys
    210                 215                 220

Val Glu Gln Leu Ser Asn Met Val Val Lys Ser Cys Lys Cys Ser
225                 230                 235

<210> SEQ ID NO 26
<211> LENGTH: 239
<212> TYPE: PRT
<213> ORGANISM: Homo sapiens

<400> SEQUENCE: 26

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95
```

```
Lys Val Glu Gln Leu Ser Asn Met Val Val Lys Ser Cys Lys Cys Ser
                100                 105                 110

Gly Gly Gly Gly Ser Gly Gly Gly Ser Gly Gly Gly Gly Ser Ala
        115                 120                 125

Leu Asp Thr Asn Tyr Cys Phe Arg Asn Leu Glu Glu Asn Cys Cys Val
        130                 135                 140

Arg Pro Leu Tyr Ile Asp Phe Arg Gln Asp Leu Gly Trp Lys Trp Val
145                 150                 155                 160

His Glu Pro Lys Gly Tyr Tyr Ala Asn Phe Cys Ser Gly Pro Cys Pro
                165                 170                 175

Tyr Leu Arg Ser Ala Asp Thr Thr His Ser Thr Val Leu Gly Leu Tyr
            180                 185                 190

Asn Thr Leu Asn Pro Glu Ala Ser Ala Ser Pro Cys Cys Val Pro Gln
        195                 200                 205

Asp Leu Glu Pro Leu Thr Ile Leu Tyr Tyr Val Gly Arg Thr Pro Lys
    210                 215                 220

Val Glu Gln Leu Ser Asn Met Val Val Lys Ser Cys Lys Cys Ser
225                 230                 235

<210> SEQ ID NO 27
<211> LENGTH: 12
<212> TYPE: PRT
<213> ORGANISM: Homo sapiens

<400> SEQUENCE: 27

Ala Glu Ala Ala Ala Lys Glu Ala Ala Ala Lys Ala
1               5                   10

<210> SEQ ID NO 28
<211> LENGTH: 20
<212> TYPE: DNA
<213> ORGANISM: Homo sapiens

<400> SEQUENCE: 28
cgtcctcgga ttctctgctc                                               20

<210> SEQ ID NO 29
<211> LENGTH: 20
<212> TYPE: DNA
<213> ORGANISM: Homo sapiens

<400> SEQUENCE: 29
gctggtgcat tttcggttgt                                               20

<210> SEQ ID NO 30
<211> LENGTH: 20
<212> TYPE: DNA
<213> ORGANISM: Homo sapiens

<400> SEQUENCE: 30
tccgcatcag gaaggctaga                                               20

<210> SEQ ID NO 31
<211> LENGTH: 19
<212> TYPE: DNA
<213> ORGANISM: Homo sapiens

<400> SEQUENCE: 31
aggaccaggc ctccaagct                                                19
```

```
<210> SEQ ID NO 32
<211> LENGTH: 22
<212> TYPE: DNA
<213> ORGANISM: Homo sapiens

<400> SEQUENCE: 32
actgacttga atgtccaacg ca                                              22

<210> SEQ ID NO 33
<211> LENGTH: 22
<212> TYPE: DNA
<213> ORGANISM: Homo sapiens

<400> SEQUENCE: 33
atctgactcc tttttcgctt cc                                              22

<210> SEQ ID NO 34
<211> LENGTH: 19
<212> TYPE: DNA
<213> ORGANISM: Homo sapiens

<400> SEQUENCE: 34
gcgtgctaat ggtggaaac                                                  19

<210> SEQ ID NO 35
<211> LENGTH: 23
<212> TYPE: DNA
<213> ORGANISM: Homo sapiens

<400> SEQUENCE: 35
cggtgacatc aaaagataac cac                                             23

<210> SEQ ID NO 36
<211> LENGTH: 20
<212> TYPE: DNA
<213> ORGANISM: Homo sapiens

<400> SEQUENCE: 36
tgcatgcatt ctcaagaggt                                                 20

<210> SEQ ID NO 37
<211> LENGTH: 20
<212> TYPE: DNA
<213> ORGANISM: Homo sapiens

<400> SEQUENCE: 37
ctatggtttt gcaggccagt                                                 20

<210> SEQ ID NO 38
<211> LENGTH: 22
<212> TYPE: DNA
<213> ORGANISM: Homo sapiens

<400> SEQUENCE: 38
cctgatcttc ctcgtgctgc tc                                              22

<210> SEQ ID NO 39
<211> LENGTH: 24
<212> TYPE: DNA
<213> ORGANISM: Homo sapiens

<400> SEQUENCE: 39
atgccaatgg acagtgttcc tctt                                            24
```

```
<210> SEQ ID NO 40
<211> LENGTH: 20
<212> TYPE: DNA
<213> ORGANISM: Homo sapiens

<400> SEQUENCE: 40
gcagcacgtg tacgagaaga                                          20

<210> SEQ ID NO 41
<211> LENGTH: 19
<212> TYPE: DNA
<213> ORGANISM: Homo sapiens

<400> SEQUENCE: 41
ggtgtcagtc tccgacgtg                                           19

<210> SEQ ID NO 42
<211> LENGTH: 22
<212> TYPE: DNA
<213> ORGANISM: Homo sapiens

<400> SEQUENCE: 42
gctgctggaa ttggtgttga tg                                       22

<210> SEQ ID NO 43
<211> LENGTH: 24
<212> TYPE: DNA
<213> ORGANISM: Homo sapiens

<400> SEQUENCE: 43
aggtgtttct ttgatgctct gtct                                     24

<210> SEQ ID NO 44
<211> LENGTH: 22
<212> TYPE: DNA
<213> ORGANISM: Homo sapiens

<400> SEQUENCE: 44
gcagcactac ttcttgacca cc                                       22

<210> SEQ ID NO 45
<211> LENGTH: 22
<212> TYPE: DNA
<213> ORGANISM: Homo sapiens

<400> SEQUENCE: 45
tctgctcctg agcattgacg tc                                       22

<210> SEQ ID NO 46
<211> LENGTH: 20
<212> TYPE: DNA
<213> ORGANISM: Homo sapiens

<400> SEQUENCE: 46
gcttcatctg tggcatcatc                                          20

<210> SEQ ID NO 47
<211> LENGTH: 20
<212> TYPE: DNA
<213> ORGANISM: Homo sapiens

<400> SEQUENCE: 47
tggaggaact ctgggaatgt                                          20
```

-continued

<210> SEQ ID NO 48
<211> LENGTH: 25
<212> TYPE: DNA
<213> ORGANISM: Homo sapiens

<400> SEQUENCE: 48
tcacccacac tgtgcccatc tacga 25

<210> SEQ ID NO 49
<211> LENGTH: 25
<212> TYPE: DNA
<213> ORGANISM: Homo sapiens

<400> SEQUENCE: 49
cagcggaacc gctcattgcc aatgg 25